(12) United States Patent
Slassi

(10) Patent No.: US 10,428,030 B2
(45) Date of Patent: Oct. 1, 2019

(54) HETEROCYCLE DERIVATIVES AND THEIR USE FOR THE TREATMENT OF CNS DISORDERS

(71) Applicant: Trillium Therapeutics Inc., Mississauga (CA)

(72) Inventor: Abdelmalik Slassi, Mississauga (CA)

(73) Assignee: Trillium Therapeutics, Mississauga (CA)

( * ) Notice: Subject to any disclaimer, the term of this patent is extended or adjusted under 35 U.S.C. 154(b) by 0 days.

(21) Appl. No.: 15/771,465

(22) PCT Filed: Oct. 31, 2016

(86) PCT No.: PCT/CA2016/051261
§ 371 (c)(1),
(2) Date: Apr. 27, 2018

(87) PCT Pub. No.: WO2017/070796
PCT Pub. Date: May 4, 2017

(65) Prior Publication Data
US 2018/0312480 A1    Nov. 1, 2018

Related U.S. Application Data

(60) Provisional application No. 62/248,350, filed on Oct. 30, 2015.

(51) Int. Cl.
| | | |
|---|---|---|
| A61K 31/538 | (2006.01) | |
| A61K 31/498 | (2006.01) | |
| A61K 31/4704 | (2006.01) | |
| C07D 265/36 | (2006.01) | |
| C07D 241/44 | (2006.01) | |
| C07D 215/227 | (2006.01) | |
| A61P 25/08 | (2006.01) | |
| A61P 25/14 | (2006.01) | |
| A61P 25/06 | (2006.01) | |
| A61P 25/28 | (2006.01) | |
| A61P 25/22 | (2006.01) | |

(52) U.S. Cl.
CPC ............ *C07D 265/36* (2013.01); *A61P 25/06* (2018.01); *A61P 25/08* (2018.01); *A61P 25/14* (2018.01); *A61P 25/22* (2018.01)

(58) Field of Classification Search
CPC ............... C07D 265/36; C07D 241/44; C07D 215/227; A61K 31/538; A61K 31/498; A61K 31/4704; A61P 25/08; A61P 25/14; A61P 25/06; A61P 25/28
USPC ...... 514/230.5, 249, 312, 314; 544/105, 235; 546/155
See application file for complete search history.

(56) References Cited

U.S. PATENT DOCUMENTS

| | | | | |
|---|---|---|---|---|
| 5,919,784 A | * | 7/1999 | Lesieur ................ | C07D 263/58 514/224.2 |
| 2005/0020591 A1 | * | 1/2005 | Su ........................ | A61K 31/498 514/234.2 |

FOREIGN PATENT DOCUMENTS

| | | | | |
|---|---|---|---|---|
| CA | 2032734 A1 | 6/1991 | | |
| CA | 2334332 A1 | 1/2000 | | |
| CA | 2492325 A1 | 2/2004 | | |
| CA | 2564199 A1 | 11/2005 | | |
| CA | 2608184 A1 | 11/2006 | | |
| CA | 2726703 A1 | 12/2009 | | |
| CA | 2750714 A1 * | 8/2010 | ........... | C07D 401/12 |
| CA | 2750714 A1 | 8/2010 | | |
| CA | 2939570 A1 | 8/2015 | | |
| JP | 05339239 A1 | 12/1993 | | |
| JP | 06316568 A | 11/1994 | | |
| WO | 2010073719 A1 | 7/2010 | | |
| WO | 2014174745 A1 | 10/2014 | | |

OTHER PUBLICATIONS

Quan et al., "Synthesis of 6-Alkyloxyl-3,4-dihydro-2(1H)-quinoliones and their anticonvulsant activities" Bull. Korean. Chem. Soc. (2005), 26 (11), pp. 1757-1760. (Year: 2005).*

Wen et al., "Synthesis and evaluation of the anti-inflammatory activity of quinoline derivatives". Med Chem Res, 2015, vol. 24, pp. 2591-2603.

Cao et al., "Synthesis and anticonvulsant activity evaluation of 7-alkoxy-2, 4-dihydro-1H-benzo[b] [1,2,4] triazolo [4,3-d] [1,4] thiazin-1-ones in various murine experimental seizure models". Med Chem Res, 2014, vol. 23, pp. 1829-1838.

Zhang et al., Synthesis and anticonvulsant activity of some 7-alkoxy-2H-1,4-benzothiazin-3(4H)-ones and 7-alkoxy-4H-[1,2,4] triazolo[4,3-d]benzo[b][1,4]thiazines, Chem. Pharm. Bull, 2010, vol. 58-(3), pp. 326-331.

(Continued)

Primary Examiner — Matthew P Coughlin
Assistant Examiner — Sagar Patel
(74) Attorney, Agent, or Firm — Bereskin & Parr LLP/S.E.N.C.R.L., s.r.l.; Patricia Folkins

(57) ABSTRACT

The present application relates to novel heterocycle derivatives of Formula (I), to processes for preparing them, pharmaceutical compositions containing them, and their use thereof in the treatment or prevention of acute and/or chronic neurological disorders such as psychosis, epilepsy, schizophrenia, Alzheimer' disease, cognitive disorders and/or memory deficits, as well as chronic and acute pain and other related CNS disorders.

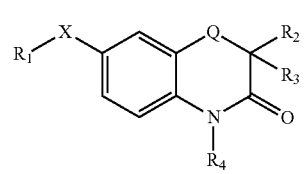

Formula (I)

17 Claims, 2 Drawing Sheets

(56) References Cited

OTHER PUBLICATIONS

Chen et al., "Copper-catalyzed cascade syntheses of 2-H-benzo[b][1,4]thiazin-3(4H)-ones and quinoxalin-2(1H)-ones through capturing S and N atom respectively from AcSH and TsNH2". J. Org. Chem., 2010, vol. 75, pp. 5768-5771.
Piao et al., "Synthesis of novel 7-benzylamino-2H-1, 4-benzoxazin-3(4H)-ones as anticonvulsant agents". European Journal of Medicinal Chemistry, 2008, vol. 43, pp. 1216-1321.
Sumida et al., "Protoporphyrinogen-IX oxidase inhibition of new diphenyl ethers". J. Pesticide Sci., 1996, vol. 21, pp. 317-321.
Sumida et al., "Synthesis of novel diphenyl ether herbicides". J. Agric. Food Chem., 1995, vol. 43, pp. 1929-1934.
Ciu et al., "Synthesis and Anticonsulvant Activity of 1-Substituted-7-Benzyloxy-4,5-dihydro-[1,2,4]triazolo[4,3-a]quinoline". Biol. Pharm. Bull, 2005, vol. 28(7), pp. 1216-1220.
Sun et al., "Design, Synthesis of 8-alkoxy-5,6-dihydro-[1,2,4]triazino[4,3-a]quinolin-1-ones with Anticonvulsant Activity", European Journal of Medicinal Chemistry, 2009, vol. 44, pp. 1265-1270.
International Preliminary Report on Patentability of corresponding PCT Application No. PCT/CA2016/051261 dated May 11, 2018.
Jin et al., "Anticonvulsant and Toxicity Evaluation of Some 7-alkoxy-4,5-dihydro-[1,2,4]triazolo[4,3-a]quinoline-1(2H)-ones". Bioorg. & Med. Chem., 2006, vol. 14, pp. 6868-6873.

\* cited by examiner

HETEROCYCLE DERIVATIVES AND THEIR USE FOR THE TREATMENT OF CNS DISORDERS

CROSS-REFERENCE TO RELATED APPLICATIONS

The present application is a national stage of co-pending international application no. PCT/CA2016/051261, filed on Oct. 31, 2016, which claims the benefit of priority from U.S. provisional patent application No. 62/248,350 filed on Oct. 30, 2015, the contents of both of which are incorporated herein by reference.

FIELD

The present application relates to novel heterocycle derivatives or compounds, to processes for preparing them, pharmaceutical compositions containing them, and their use thereof, for example, in the treatment or prevention of acute and/or chronic neurological disorders such as psychosis, epilepsy, schizophrenia, Alzheimer disease, cognitive disorders and memory deficits, as well as chronic and acute pain and other related CNS disorders.

BACKGROUND

Epilepsy is a complex neurological disorder that affects ~50 million people worldwide. The lifetime prevalence is ~1%, and it affects individuals of all ages regardless of gender or socio-economic status. Epilepsy can be acquired as a result of an insult to the brain such as trauma, infection, stroke or a tumour, or can result from a genetic mutation in one or more of the ion channel or neurotransmitter genes or proteins that control brain excitability (Bialer et al. *Nat. Rev. Drug Discov.* 2010, 9:68-82).

Epileptic seizures can be generalized (generalized epileptic seizure), originating in both hemispheres of the brain simultaneously, or partial (focal seizures) originating in one or more parts of one or both hemispheres, most commonly the temporal lobe. With generalized seizures, consciousness is always impaired or lost. Consciousness may be maintained in partial seizures but partial seizures may become generalized seizures in a process referred to as secondary generalization, at which point consciousness is lost. In patients the type of epilepsy or epileptic syndrome are further classified according to features such as the type of seizure, etiology, age of onset and electroencephalogram. Epilepsy or epileptic syndromes can be either idiopathic (etiology or cause is unknown) with a presumed genetic basis or symptomatic (acquired). The known potential causes of epilepsy include brain tumors, infections, traumatic head injuries, perinatal insults, developmental malformations, cerebrovascular diseases, febrile seizures and status epilepticus (Loscher, *Trends Pharmacol. Sci,* 2002, 23:113-118).

Despite progress in understanding the pathogenesis of epileptic seizures, the cellular basis of human epilepsy remains a mystery and, in the absence of specific etiological comprehension, approaches to drug therapy are still directed toward the control of symptoms, i.e., suppression of seizures. Chronic administration of antiepileptic drugs (AEDs) is the treatment of choice in epilepsy (Dreyfuss et al. *Handbook of Experimental Pharmacology*; Springer: Berlin, 1999; 1-15).

The past decade witnessed considerable progress in the pharmacotherapy of epilepsy, including the introduction of several new AEDs and improved formulations of older, "first-generation" drugs, such as phenytoin, carbamazepine, phenobarbital, and valproate. Newer "second-generation" drugs include lamotrigine, vigabatrin, tiagabine, topiramate, oxcarbazepine, zonisamide, gabapentin, and levetiracetam. However, only a minority of patients refractory to first-generation AEDs are reported to be seizure-free with second-generation AEDs.

A number of clinical anticonvulsants including phenytoin, carbamazepine, lamotrigine, gabapentin and pregabalin are widely utilized in the management of neuropathic pain (Collins et al. *Expert Opinion Emerging Drugs,* 2005, 10:95-108). Neuropathic pain results from a cascade of neurobiological events, which tend to induce electrical hyper excitability within somatosensory conduction pathway. Since electrical hyper excitability is also the hallmark of epileptic seizure activity, anticonvulsants are among the first agents adopted in the treatment of neuropathic pain and remain the first option in clinical use.

Pain is both a sensory and emotional experience, and is generally associated with tissue damage or inflammation. Typically, pain is divided into two general categories—acute pain and chronic pain. Both differ in their etiology, pathophysiology, diagnosis, and most importantly treatment.

Acute pain is short term, and is typically of readily identifiable cause. Patients suffering from acute pain typically respond well to medications. In contrast, chronic pain—medically defined as pain that lasts for 3-6 months or longer, is often not associated with any obvious injury; indeed, patients can suffer from protracted pain that persists for months or years after the initial insult. Whilst acute pain is generally favorably treated with medications, chronic pain is often much more difficult to treat, generally requiring expert care. Few, if any, ethical drugs have been prospectively developed for the treatment of chronic pain. Instead, the current medications used to treat chronic pain are "borrowed" from other diseases, most commonly antiepileptic drugs and antidepressants.

Current first-line treatments for chronic pain include opioids, analgesics such as gabapentin, and tricyclic antidepressants. When opioids are administered over prolonged periods, undesirable side effects such as drug tolerance, chemical dependency and even physiological addiction can occur. Of treatment remedies currently available for chronic pain, at best approximately 30% are effective in significantly diminishing the pain, and these can lose their efficiency over time.

In instances in which treatment with a single agent proves to be unsuccessful, combination therapy is often then explored as a second line treatment. For example, such combination therapy may employ administration of an opioid agent with an adjuvant analgesic, although the relative doses of each are often subject to prolonged trial and error periods. Often, triple drug therapy is necessary. Such therapy generally involves a combination of tricyclic antidepressants, anticonvulsants and a systemic local anesthetic. Patient compliance drops significantly, however, when treatment requires the administration of multiple pharmacologic agents. Recently, researchers reported the use of a combination of morphine and gabapentin in a randomized study for controlling nerve pain (Gilron, et al., *N. Eng. J. Med.,* 2005, 352:1281-82).

In treatment, it is important to consider overall pain relief, as well as the type of pain relief. For example, chronic pain is typically viewed as allodynia or hyperalgesia. Allodynia is pain sensation from a stimulus which is not normally painful. Allodynia is typically caused by a physical stimulus and is thus referred to as tactile or mechanical allodynia. Hyperalgesia is an exaggerated sensation form a stimulus which is normally painful. The hyperalgesia can occur from a variety of stimuli but, commonly, a patient's reaction to hot or cold stimuli is reported.

Neuropathic pain (NP) is generally thought of as a maladaptive chronic condition in which pain originates from damaged nerves, often yielding pain that is out of proportion to the extent of any injury. Damage can occur from a physical injury such as trauma or from chemical injury such as chemotherapeutics (e.g. paclitaxel). Neuropathic pain of this type is an important component of a number of syndromes of varying etiologies whose common characteristic is the development of a prolonged and profound pain state. Among these conditions are spinal cord injury, post-herpetic neuralgia, diabetic neuropathy, phantom limb pain, stump/neuroma pain, post-ischemic pain (stroke), fibromyalgia, complex regional pain syndrome (CRPS), chemotherapy-induced neuropathic pain, vertebral disk rapture, trigeminal neuralgia and others.

Recently, it has been recognized that neuropathic pain can also manifest itself in the absence of an identifiable nerve injury. These indications include AIDS and mirror image pain. The lack of any nerve injury but unmistakable chronic pain has led to increased interest in the role of glial cells in the maintenance of the neuropathic pain state (Watkins and Maier, *Drug Disc. Today: Ther. Strategies* 2004, 1:83-88; Watkins and Maier, *Nat. Rev. Drug Discovery* 2003, 2:973-985). More specifically, recent research has demonstrated that glial cells enhance the release of neurotransmitters which relay pain information to the spinal cord and, even more strikingly, release substances which increase the excitability of pain-responsive neurons in the spinal cord. These substances, called pro-inflammatory cytokines, create and maintain exaggerated or pathological pain responses (Wieseler-Frank et al., *Neurosignals* 2005, 14:166-174). Blocking the activation of glial cells reduces pro-inflammatory cytokines and reverses pathological pain. To date, no therapeutics have been approved which have a putative glial cell-attenuation mechanism for the treatment of neuropathic pain. Molecules which are glial cell-attenuators may play an important role in the treatment of neuropathic pain.

In light of the above shortcomings in current approaches for treating chronic pain there exists a need for improved compositions and methods for treating pain, particularly neuropathic pain and its associated symptoms and, more specifically, neuropathic pain associated with certain conditions such as fibromyalgia, among others. Such approaches should ideally overcome one or more of the problems associated with existing methods for treating chronic pain.

Migraine is a disease condition characterized by episodes of head pain that is often throbbing and frequently unilateral, and can be severe. In migraine without aura, attacks are usually associated with nausea, vomiting or sensitivity to light, sound or movement. In some patients, migraine attacks are usually preceded or accompanied by transient focal neurological symptoms, which are usually visual; such patients are described as having migraine with aura.

Both migraine and epilepsy are usually included in the spectrum of neurological chronic disorders with episodic manifestations that are known to be characterized by recurrent attacks of nervous system dysfunction with a return to baseline between attacks.

The hypothesis of a possible clinical continuum between migraine and epileptic syndromes as entities resulting from altered neuronal excitability with a similar genetic basis has been postulated (Haut et al. *Lancet Neurol* 2006, 5:148-157).

Epilepsy is a comorbid condition of migraine; it occurs more commonly in patients with migraine than in the general population, and the prevalence of migraine in epileptic patients is higher than in controls.

Some antiepileptic drugs (AEDs) are effective in the prevention of migraine (Rogawski et al *Nat. Med.* 2004, 10:685-692; Silberstein, S. D., *Trends Pharmacol. Sci.* 2006, 27:410-415). A rationale for this use is the hypothesis that migraine and epilepsy share several pathogenetic mechanisms.

Anxiety is broadly defined as a state of unwarranted or inappropriate worry often accompanied by restlessness, tension, distraction, irritability and sleep disturbances. This disproportionate response to environmental stimuli can hyper activate the hypothalamic-pituitary-adrenal axis and the autonomic nervous system, resulting in somatic manifestation of anxiety, including shortness of breath, sweating, nausea, rapid heartbeat and elevated blood pressure (Sanford et al. *Pharmacol. Ther.* 2000, 88:197-212). Anxiety disorders represent a range of conditions and as a result have been classified into multiple distinct conditions, including generalized anxiety disorder (GAD), panic attack, post-traumatic stress disorder (PTSD), obsessive compulsive disorder (OCD) and social phobias (Sanford et al. *Acta. Psychiatr. Scand. Suppl.* 1998, 393:74-80).

Generalized anxiety disorder (GAD) is the most common of the anxiety disorders and is characterized by excessive and persistent worries. Some of the specific symptoms of GAD include restlessness, motor tension, difficulty concentrating, irritability, and sleep disturbances and the severity of the symptoms over time may be linked to the changing nature of the environmental stressor. With age, GAD symptoms become less severe.

Panic Disorder is a well-studied psychiatric condition that consists of multiple disabling panic attacks characterized by and intense autonomic arousal. In addition, heightened fear and anxiety states occur both during and between panic attacks. Approximately 3% of woman and 1.5% of men have panic attacks. During a panic attack, the individual experiences multiple symptoms including light-headedness, a pounding heart and difficulty in breathing. Panic disorder may be caused by an oversensitive brain system regulating autonomic functions.

Post-traumatic stress disorder (PTSD) is another example of a disorder associated with intense fear and anxiety states that require psychiatric treatment. PTSD results from exposure to a life threatening or traumatic event. Individuals with PTSD have recurring thoughts of the terrifying event. Reenactment of the event varies in duration from a few seconds or hours to several days. Individuals with major depression, with panic disorders or lacking strong social supports are vulnerable to develop PTSD.

Anxiety disorders, which occur in 10% to 30% of the population, represent not only a significant public health issue but place a substantial economic burden on society. A number of drugs have either been developed or are being developed for treating the different subclasses of anxiety. Some of these agents such as tricyclic antidepressants and β-adrenoreceptor antagonists found either limited use in treating specific disorders such as performance anxiety (e.g. β-adrenoreceptor antagonists suppression of the sympathetic manifestations of anxiety) or have fallen out of favor for reasons of efficacy and/or safety. Currently, direct and indirect serotonin receptor agonists (e.g. selective serotonin reuptake inhibitors (SSRI) and buspirone) and benzodiazepines are most often prescribed for treating anxiety disorders with benzodiazepine receptor agonist being a preferred therapeutic modality. The ability of benzodiazepines to enhance γ-aminobutyric acid (GABA) neurotransmission safely and rapidly is central to their effectiveness in treating anxiety disorder especially GAD and panic disorders (Stahl et al. *J. Clin. Psychiatry* 2002, 63: 756-757). Benzodiazepines act by positively modulating the inhibitory neurotransmitter GABA through an allosteric site on the GABA A receptor complex, a ligand-gated chloride ion channel. Nonetheless, the use of benzodiazepines is limited by side effects associated with enhanced GABAnergic neurotransmission, manifesting as sedation, muscle relaxation, amnesia and ataxia. Moreover, the potential for abuse and physical dependence is associated with the long-term use of benzodiazepines.

The following compound was reported to be active in the mouse electroshock seizure (MES) and pentylenetetrazole (PTZ) models of epilepsy (Bioorg. Med. Chem 2006; 14 (20), 6868; Eur. J. Med. Chem 2009; 44 (3), 1265):

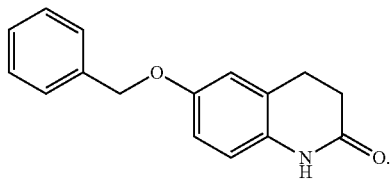 [SMILES: O=C1CCc2cc(OCc3ccccc3)ccc2N1]

SUMMARY

The compounds of this application were strategically designed with the objective of identifying a broad spectrum antiepileptic drug (AED) with a favorable safety and tolerability profile. A broad spectrum profile could distinguish these compounds not only from other first-generation AED such as phenytoin (PHT) and carbamazepine (CBZ) but also from many of the second-generation compounds such as pregabalin and levetiracetam. In preclinical studies, compounds that demonstrate broad anticonvulsant activity in acute rodent seizure models of electroshock and chemical origin (e.g. MES and PTZ) may show efficacy in suppressing spike and wave discharges in models of generalized absence epilepsy. Furthermore, the compounds of this application were designed to have potential therapeutic applications beyond epilepsy.

The present application relates to novel heterocycle derivatives or compounds, to processes for preparing them, pharmaceutical compositions containing them, and uses thereof in the treatment or prevention of acute and/or chronic neurological disorders such as psychosis, epilepsy, schizophrenia, Alzheimer' disease, cognitive disorders and memory deficits, as well as chronic and acute pain and other related CNS disorders.

It is an object of the present application to provide compounds and compositions useful for the treatment of a CNS disorder such as epilepsy, pain, or an anxiety disorder.

In one aspect, there is provided a compound of Formula (I), or a pharmaceutically acceptable salt, solvate, tautomer or optical isomer, or combination thereof:

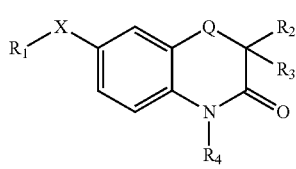

Formula (I)

wherein:

$R_1$ is selected from the group consisting of $C_1$-$C_6$ lower alkyl, $C_1$-$C_6$ lower alkoxy, $C_1$-$C_6$ lower alkyl-ester, $C_1$-$C_6$ lower alkyl-amide, $C_1$-$C_6$ lower alkyl-acid, $C_1$-$C_6$ lower haloalkyl, $C_1$-$C_6$-lower haloalkoxy, $C_1$-$C_6$-lower haloalkyl-ester, cycloalkyl, heterocycloalkyl, bicycloalkyl, heterobicycloalkyl, aryl, heteroaryl, alkylene-aryl, alkylene-heteroaryl, hydroxyalkyl, hydroxycycloalkyl, hydroxy-heterocycloalkyl, alkenyl, aryl-alkenyl, heteroaryl-alkenyl, alkynyl, aryl-alkynyl, cycloalkenyl, heterocycloalkenyl, alkylene-O-alkyl, alkylene-O-cycloalkyl, alkylene-O-heterocycloalkyl, and alkylene-O-alkylene-cycloalkyl, alkylene-O-alkylene-heterocycloalkyl, each $R_1$ group being optionally substituted with one or more independently-selected groups $R_5$;

$R_2$ and $R_3$ are each independently selected from the group consisting of hydrogen, halogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl; or $R_2$ and $R_3$ connect to form, together with the carbon atom to which they are attached, a three to seven-membered carbocyclic or heterocyclic ring; and $R_4$ is selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl;

X and Q are independently selected from $CH_2$, O, $NR_7$, S, SO and $SO_2$;

$R_5$ is selected from the group consisting of hydroxy, halogen, cyano, nitro, $CO_2R_6$, $CONHR_6$, $CON(R_6)_2$, $SO_2NHR_6$, $SO_2N(R_6)_2$, $C_1$-$C_6$ lower alkyl, $C_1$-$C_6$ lower alkoxy, $C_1$-$C_6$ lower alkyl-ester, $C_1$-$C_6$ lower alkyl-amide, $C_1$-$C_6$ lower alkyl-acid, $C_1$-$C_6$ lower haloalkyl, $C_1$-$C_6$ lower haloalkoxy, $C_1$-$C_6$ lower haloalkyl-ester, cycloalkyl, heterocycloalkyl, bicycloalkyl, heterobicycloalkyl, aryl, heteroaryl, hydroxyalkyl, hydroxycycloalkyl, hydroxy-heterocycloalkyl, cyanoalkyl, alkenyl, alkynyl, cycloalkenyl, heterocycloalkenyl, alkylenearyl, alkyleneheteroaryl, alkylene-O-alkyl, alkylene-O-cycloalkyl, alkylene-O-heterocycloalkyl, alkylene-O-alkylene-cycloalkyl and alkylene-O-alkylene-heterocycloalkyl; and $R_6$ and $R_7$ are independently selected from the group consisting of H, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl, provided that at least one of $R_1$, $R_2$ and $R_3$ comprises a fluorine atom.

In some embodiments, the present application includes a compound of Formula (I), or a pharmaceutically acceptable salt, solvate, tautomer or optical isomer, or combination thereof:

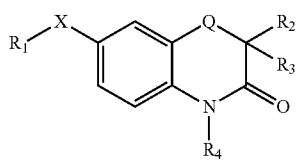

Formula (I)

wherein:
R$_1$ is selected from the group consisting of C$_1$-C$_6$alkyl, C$_1$-C$_6$cycloalkyl, heterocycloalkyl, aryl, heteroaryl, C$_1$-C$_6$alkylene-aryl, C$_1$-C$_6$alkylene-heteroaryl, C$_2$-C$_6$alkenyl, C$_2$-C$_6$alkenylenearyl, C$_2$-C$_6$alkenyleneheteroaryl, C$_2$-C$_6$alkynyl, C$_2$-C$_6$alkynylene-aryl, C$_3$-C$_{12}$cycloalkenyl, heterocycloalkenyl, C$_1$-C$_6$alkylene-O—C$_1$-C$_6$alkyl, C$_1$-C$_6$alkylene-O—C$_3$-C$_{12}$cycloalkyl, C$_1$-C$_6$alkylene-O-heterocycloalkyl, C$_1$-C$_6$alkylene-O—C$_1$-C$_6$alkylene-C$_3$-C$_{12}$cycloalkyl and C$_1$-C$_6$alkylene-O—C$_1$-C$_6$alkylene-heterocycloalkyl, each R$_1$ group being optionally substituted with one or more independently-selected groups R$_5$;
R$_2$ and R$_3$ are each independently selected from the group consisting of hydrogen, halogen, C$_1$-C$_6$alkyl, C$_2$-C$_6$alkenyl, C$_2$-C$_6$alkynyl, C$_1$-C$_6$haloalkyl, C$_3$-C$_{12}$cycloalkyl, heterocycloalkyl, aryl and heteroaryl; or
R$_2$ and R$_3$ connect to form, together with the carbon atom to which they are attached, a three to seven-membered carbocyclic or heterocyclic ring; and
R$_4$ is selected from the group consisting of hydrogen, C$_1$-C$_6$alkyl, C$_2$-C$_6$alkenyl, C$_2$-C$_6$alkynyl, C$_1$-C$_6$haloalkyl, C$_3$-C$_{12}$cycloalkyl, heterocycloalkyl, aryl and heteroaryl;
X and Q are independently selected from CH$_2$, O, NR$_7$, S, SO and SO$_2$;
R$_5$ is selected from the group consisting of hydroxy, halogen, cyano, nitro, CO$_2$R$_6$, CONHR$_6$, CON(R$_6$)$_2$, SO$_2$NHR$_6$, SO$_2$N(R$_6$)$_2$, C$_1$-C$_6$alkyl, C$_1$-C$_6$alkoxy, C$_1$-C$_6$alkyl-ester, C$_1$-C$_6$alkyl-amide, C$_1$-C$_6$alkyl-acid, C$_1$-C$_6$haloalkyl, C$_1$-C$_6$haloalkoxy, C$_1$-C$_6$haloalkyl-ester, C$_3$-C$_{12}$cycloalkyl, heterocycloalkyl, aryl, heteroaryl, C$_1$-C$_6$hydroxyalkyl, C$_3$-C$_{12}$hydroxycycloalkyl, hydroxy-heterocycloalkyl, C$_1$-C$_6$cyanoalkyl, C$_2$-C$_6$alkenyl, C$_2$-C$_6$alkynyl, C$_3$-C$_{12}$cycloalkenyl, heterocycloalkenyl, C$_1$-C$_6$alkylenearyl, C$_1$-C$_6$alkyleneheteroaryl, C$_1$-C$_6$alkylene-O—C$_1$-C$_6$alkyl, C$_1$-C$_6$alkylene-O—C$_3$-C$_{12}$cycloalkyl, C$_1$-C$_6$alkylene-O-heterocycloalkyl, C$_1$-C$_6$alkylene-O—C$_1$-C$_6$alkylene-C$_3$-C$_{12}$cycloalkyl and C$_1$-C$_6$alkylene-O—C$_1$-C$_6$alkylene-heterocycloalkyl; and
R$_6$ and R$_7$ are independently selected from the group consisting of hydrogen, C$_1$-C$_6$alkyl, C$_2$-C$_6$alkenyl, C$_2$-C$_6$alkynyl, C$_1$-C$_6$haloalkyl, C$_3$-C$_{12}$cycloalkyl, heterocycloalkyl, aryl and heteroaryl,
provided that at least one of R$_1$, R$_2$ and R$_3$ comprises a fluorine atom.

In some embodiments, R$_1$ comprises a difluoromethoxy or a trifluoromethoxy substituent. In some embodiments, R$_2$ and R$_3$ are both H.

In one aspect, there is provided a compound of Formula (I):

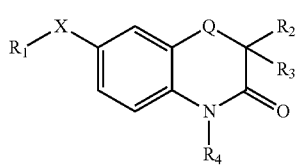

Formula (I)

wherein:
R$_1$ is selected from the group consisting of C$_1$-C$_6$-lower alkyl, C$_1$-C$_6$-lower alkoxy, C$_1$-C$_6$-lower alkyl-ester, C$_1$-C$_6$-lower alkyl-amide, C$_1$-C$_6$-lower alkyl-acid, C$_1$-C$_6$-lower haloalkyl, C$_1$-C$_6$-lower haloalkoxy, C$_1$-C$_6$-lower haloalkyl-ester, cycloalkyl, heterocycloalkyl, bicycloalkyl, heterobicycloalkyl, aryl, heteroaryl, alkyl-aryl, alkyl-heteroaryl, hydroxyalkyl, hydroxycycloalkyl, hydroxy-heterocycloalkyl, alkenyl, aryl-alkenyl, heteroaryl-alkenyl, alkynyl, aryl-alkynyl, heteroary-alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl, optionally substituted with one or more independently-selected groups R$_5$; wherein R$_5$ selected from the group consisting of H, hydroxy, halogen, cyano, nitro, CO$_2$R$_6$, CONHR$_6$, CON(R$_6$)$_2$, SO$_2$NHR$_6$, SO$_2$N(R$_6$)$_2$, C$_1$-C$_6$-lower alkyl, C$_1$-C$_6$-lower alkoxy, C$_1$-C$_6$-lower alkyl-ester, C$_1$-C$_6$-lower alkyl-amide, C$_1$-C$_6$-lower alkyl-acid C$_1$- to C$_6$-lower haloalkyl, C$_1$-C$_6$-lower haloalkoxy, C$_1$-C$_6$-lower haloalkyl-ester, cycloalkyl, heterocycloalkyl, bicycloalkyl, heterobicycloalkyl, aryl, heteroaryl, aryl, heteroaryl, hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl;
R$_2$ and R$_3$ are each independently selected from the group consisting of hydrogen, halogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl; or
R$_2$ and R$_3$ connect to form a three to seven-membered ring; and
R$_4$ is selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl; and
X and Q are independently selected from C, O, NR$_7$, S, SO and SO$_2$, wherein R$_7$ is selected from the groups consisting of H, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl.

In another aspect, R$_1$ is optionally substituted with one or more independently-selected groups R$_8$ and R$_8$ is selected from the group consisting of OH, CN, halo, alkyl, alkoxy, haloalkyl, haloalkoxy, cycloalkyl, heterocycloalkyl, C(O)R$_7$, C(O)OR$_9$, SO$_2$R$_9$ and C(O)NR$_{10}$R$_{11}$; wherein R$_9$, R$_{10}$ and R$_{11}$ are independently selected from the group consisting of H, alkyl, cycloalkyl, heterocycloalkyl, aryl and heteroaryl. In yet a further aspect, R$_2$ and R$_3$ are independently selected from the group consisting of H, halogen, substituted or unsubstituted haloalkyl, substituted or unsubstituted alkyl, substituted or unsubstituted cycloalkyl, and substituted or unsubstituted heterocycloalkyl.

In a specific aspect, R$_1$ is a substituted alkyl-aryl or alkyl-heteroaryl, and R$_2$ and R$_3$ are independently selected from hydrogen, halogen or lower alkyl, and $R_4$ is selected from hydrogen and lower alkyl.

In a more specific aspect, $R_1$ is substituted with one or more independently-selected groups $R_6$, wherein $R_6$ is selected from halo and haloalkyl, and $R_4$ is hydrogen.

In yet another aspect, there is provided a pharmaceutical composition comprising a compound of Formula (I) and at least one pharmaceutically acceptable carrier and/or excipient. In a further aspect, the carrier is a pharmaceutically-acceptable carrier.

In another aspect, there is provided a pharmaceutical composition comprising therapeutically effective amount of a compound of Formula (I) to treat medical conditions such as epilepsy, neuropathic pain, acute and chronic inflammatory pain, migraine, tardive dyskinesia, anxiety and other related CNS disorders; such compositions can comprise a compound of Formula (I) in association with one or more pharmaceutically acceptable diluents, excipients and/or inert carriers.

In yet another aspect there is provided a method for treating at least one of epilepsy, neuropathic pain, acute and chronic inflammatory pain, migraine, tardive dyskinesia, anxiety and other related CNS disorders in a mammal, comprising administering to the mammal a therapeutically effective amount of a compound or composition noted above. In a further aspect, the mammal is a human. In still a further aspect, the compound or composition is administered orally and/or parenterally. In yet another aspect, the compound or composition is administered intravenously and/or intraperitoneally.

In yet a further aspect there is provided the use of the compound or composition noted above for manufacture of a medicament for treatment of at least one of epilepsy, neuropathic pain, acute and chronic inflammatory pain, migraine, tardive dyskinesia, anxiety and other related CNS disorders. In yet a further aspect there is provided the use of the compound or composition noted above for treatment of at least one of epilepsy, neuropathic pain, acute and chronic inflammatory pain, migraine, tardive dyskinesia, anxiety and other related CNS disorders in a mammal. In a further aspect, the mammal is a human. In still a further aspect, the compound or composition is administrable orally and/or parenterally. In yet another aspect, the compound or composition is administrable intravenously and/or intraperitoneally.

In another aspect, there is provided use of the compound of Formula (I) in the treatment of epilepsy, neuropathic pain, acute and chronic inflammatory pain, migraine, tardive dyskinesia, anxiety and other related CNS disorders.

The application additionally provides a process for the preparation of compounds of Formula (I). General and specific processes are discussed in more detail set forth in the Examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DETAILED DESCRIPTION

I. Definitions

Figure 1:
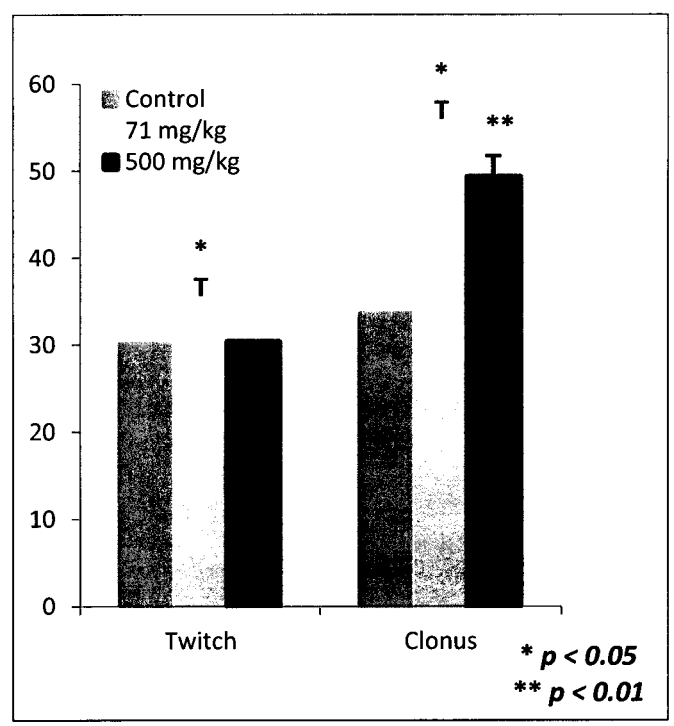
FIG. 1 shows the effect of compound 3 in an Intravenous Metrazol Seizure Threshold Test in a mouse.
Figure 2:
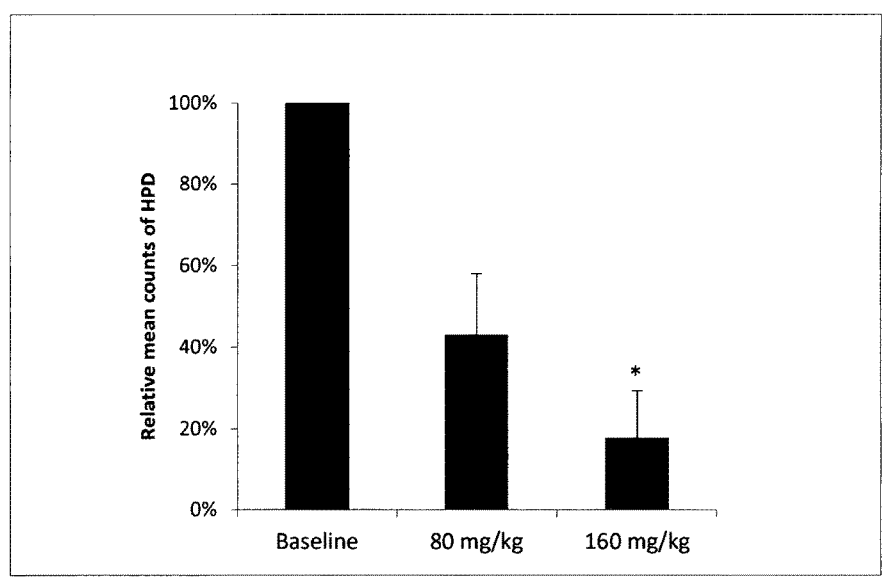
FIG. 2 shows the effect of compound 3 on Hippocampal Paroxysmal Discharges (HPD) in Mice 4 Weeks after Unilateral Intrahippocampal KA Injection.

Unless otherwise indicated, the definitions and embodiments described in this and other sections are intended to be applicable to all embodiments and aspects of the present application herein described for which they are suitable as would be understood by a person skilled in the art.

Unless specified otherwise within this specification, the nomenclature used in this specification generally follows the examples and rules stated in "Nomenclature of Organic chemistry" (Pergamon Press, 1979), Sections A, B, C, D, E, F, and H. Optionally, a name of a compound may be generated using a chemical naming program: ACD/ChemSketch, Version 5.09/September 2001, Advanced Chemistry Development, Inc., Toronto, Canada.

The term "$C_m$-$C_n$" or "$C_m$-$C_n$ group" used alone or as a prefix, refers to any group having m to n carbon atoms, wherein m and n are 0 or positive integers, and n>m. For example, "$C_1$-$C_6$" would refer to a chemical group having 1 to 6 carbon atoms.

The term "group" and "radical" are used interchangeably herein.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. The term "lower alkyl" as used herein refers to an alkyl group having 1 to 6 carbon atoms.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising at least 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to links two structures together.

The term "heterocycle," used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroalkyl," used alone or as a suffix or prefix, refers to a radical formed as a result of replacing one or more carbon atom of an alkyl with one or more heteroatoms selected from N, O and S.

The term "heteroaromatic," used alone or as a suffix or prefix, refers to a ring-containing structure or molecule having one or more multivalent heteroatoms, independently selected from N, O and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers to a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms, where 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

As a prefix, "substituted" refers to a structure, molecule or group in which one or more hydrogens are replaced with one or more $C_{1-12}$hydrocarbon groups or with one or more chemical groups that contain one or more heteroatoms selected from N, O, S, F, Cl, Br, I, and P. Exemplary chemical groups containing one or more heteroatoms include heterocyclyl, —$NO_2$, —OR, —R'OR, —Cl, —Br, —I, —F, —$CF_3$, —C(=O)R, —C(=O)OH, —$NH_2$, —SH, —NHR, —$NR_2$, —SR, —$SO_3$H, —$SO_2$R, —S(=O)R, —CN, —OH, —C(=O)OR, —C(=O)$NR_2$, —NRC(=O) R, —NRC(=O)OR, —R'$NR_2$, oxo (=O), imino (=NR), thio (=S), and oximino (=N—OR), wherein each "R" is hydrogen or a $C_{1-12}$hydrocarbyl and "R'" is a $C_{1-12}$hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

As a suffix, "substituted" used in relation to a first structure, molecule or group, followed by one or more names of chemical groups, refers to a second structure, molecule or group that results from replacing one or more hydrogens of the first structure, molecule or group with the one or more named chemical groups. Thus, a "phenyl substituted by nitro" refers to nitrophenyl.

The term "optionally substituted" refers to groups, structures, or molecules that are either substituted or not substituted.

It is understood that substituents and substitution patterns on the compounds of the application may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon or on different carbons, as long as a stable structure results.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran, tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy," used alone or as a suffix or prefix, refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino," used alone or as a suffix or prefix, refers to radicals of the general formula —NRR', wherein R and R' are independently selected from hydrogen or a hydrocarbon radical.

Used alone or as a prefix or suffix, "acyl" means the group —C(=O)—R, wherein R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

The term "$C_1$-$C_6$-lower alkyl-ester" as used herein means the group $C_1$-$C_6$alkylene-C(=O)—OR, wherein R is an optionally substituted hydrocarbyl.

The term "$C_1$-$C_6$-lower alkyl-amide" as used herein means the group $C_1$-$C_6$alkylene-C(=O)—NRR', wherein R and R' are independently, H or an optionally substituted hydrocarbyl.

The term "$C_1$-$C_6$-lower alkyl-acid" as used herein means the group $C_1$-$C_6$alkylene-C(=O)—OH.

"Halogen" includes fluorine, chlorine, bromine and iodine.

"Halogenated," used as a prefix of a group, means one or more hydrogens on the group is replaced with one or more halogens.

A first ring group being "fused" with a second ring group means the first ring and the second ring share at least two atoms there between.

"Link," "linked," or "linking," unless otherwise specified, means covalently linked or bonded.

The term "compound(s) of the application" or "compound(s) of the present application" as used herein means a compound of Formula (I), or a pharmaceutically acceptable salt, hydrate, solvate, isoform, tautomer, optical isomer, or combination thereof.

The term "composition(s) of the application" or "composition(s) of the present application" as used herein means a composition comprising at least one compound of the application and at least one an additional component, such as a carrier.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula (I) or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, or such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula (I) for laboratory use, or for subsequent conversion to a pharmaceutically acceptable acid addition salt.

A "pharmaceutically acceptable basic addition salt" is any non-toxic organic or inorganic base addition salt of the acid compounds represented by Formula (I) or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that ester functionality, if any, elsewhere in the molecule is not hydrolyzed. The selection criteria for the appropriate salt will be known to one skilled in the art.

"Solvate" means a compound of Formula (I) or the pharmaceutically acceptable salt of a compound of Formula (I) wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral center that are not mirror images of one another (diastereomers).

"Patient" for the purposes of the present application includes humans and other animals, particularly mammals, and other organisms. Thus the methods are applicable to both human therapy and veterinary applications. In an embodiment the patient is a mammal, and in a another embodiment the patient is human.

"Therapeutically effective amount" is an amount of a compound of the application, that when administered to a patient, ameliorates a symptom of the disease. The amount of a compound of the application which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound of the application, such as the compound of Formula (I), which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

In embodiments comprising an "additional" or "second" component or element, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present. The term "and/or" with respect to pharmaceutically acceptable salts, solvates and/or radiolabeled versions thereof means that the compounds of the application exist as individual salts, hydrates or radiolabeled versions, as well as a combination of, for example, a salt of a solvate of a compound of the application or a salt of a radiolabeled version of a compound of the application.

In understanding the scope of the present application, the term "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements, or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of" as used herein is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "available", as in "available hydrogen atoms" or "available atoms" refers to atoms that would be known to a person skilled in the art to be capable of replacement by another atom or substituent.

II. Compounds and Compositions of the Application

One embodiment of the application includes a compound of Formula (I), or a pharmaceutically acceptable salt, solvate, tautomer or optical isomer, or combination thereof:

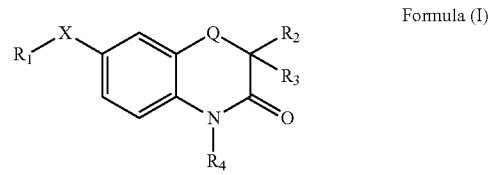

Formula (I)

wherein:
$R_1$ is selected from the group consisting of $C_1$-$C_6$ lower alkyl, $C_1$-$C_6$ lower alkoxy, $C_1$-$C_6$ lower alkyl-ester, $C_1$-$C_6$ lower alkyl-amide, $C_1$-$C_6$ lower alkyl-acid, $C_1$-$C_6$ lower haloalkyl, $C_1$-$C_6$-lower haloalkoxy, $C_1$-$C_6$-lower haloalkyl-ester, cycloalkyl, heterocycloalkyl, bicycloalkyl, heterobicycloalkyl, aryl, heteroaryl, alkylene-aryl, alkylene-heteroaryl, hydroxyalkyl, hydroxycycloalkyl, hydroxyheterocycloalkyl, alkenyl, aryl-alkenyl, heteroaryl-alkenyl, alkynyl, aryl-alkynyl, cycloalkenyl, heterocycloalkenyl, alkylene-O-alkyl, alkylene-O-cycloalkyl, alkylene-O-heterocycloalkyl, and alkylene-O-alkylene-cycloalkyl, alkylene-O-alkylene-heterocycloalkyl, each $R_1$ group being optionally substituted with one or more independently-selected groups $R_5$;

$R_2$ and $R_3$ are each independently selected from the group consisting of hydrogen, halogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl; or $R_2$ and $R_3$ connect to form, together with the carbon atom to which they are attached, a three to seven-membered carbocyclic or heterocyclic ring; and $R_4$ is selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl;

X and Q are independently selected from $CH_2$, O, $NR_7$, S, SO and $SO_2$;

$R_5$ is selected from the group consisting of hydroxy, halogen, cyano, nitro, $CO_2R_6$, $CONHR_6$, $CON(R_6)_2$, $SO_2NHR_6$, $SO_2N(R_6)_2$, $C_1$-$C_6$ lower alkyl, $C_1$-$C_6$ lower alkoxy, $C_1$-$C_6$ lower alkyl-ester, $C_1$-$C_6$ lower alkyl-amide, $C_1$-$C_6$ lower alkyl-acid, $C_1$-$C_6$ lower haloalkyl, $C_1$-$C_6$ lower haloalkoxy, $C_1$-$C_6$ lower haloalkyl-ester, cycloalkyl, heterocycloalkyl, bicycloalkyl, heterobicycloalkyl, aryl, heteroaryl, hydroxyalkyl, hydroxycycloalkyl, hydroxy-heterocycloalkyl, cyanoalkyl, alkenyl, alkynyl, cycloalkenyl, heterocycloalkenyl, alkylenearyl, alkyleneheteroaryl, alkylene-O-alkyl, alkylene-O-cycloalkyl, alkylene-O-heterocycloalkyl, alkylene-O-alkylene-cycloalkyl and alkylene-O-alkylene-heterocycloalkyl; and $R_6$ and $R_7$ are independently selected from the group consisting of H, substituted or unsubstituted alkyl, substituted or unsubstituted alkenyl, substituted or unsubstituted alkynyl, substituted or unsubstituted haolalkyl, substituted or unsubstituted cycloalkyl, substituted or unsubstituted heterocycloalkyl, substituted or unsubstituted aryl, and substituted or unsubstituted heteroaryl, provided that at least one of $R_1$, $R_2$ and $R_3$ comprises a fluorine atom.

In some embodiments, the present application includes a compound of Formula (I), or a pharmaceutically acceptable salt, solvate, tautomer or optical isomer, or combination thereof:

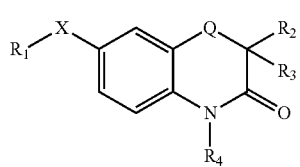

Formula (I)

wherein:

$R_1$ is selected from the group consisting of $C_1$-$C_6$alkyl, $C_1$-$C_6$cycloalkyl, heterocycloalkyl, aryl, heteroaryl, $C_1$-$C_6$alkylene-aryl, $C_1$-$C_6$alkylene-heteroaryl, $C_2$-$C_6$alkenyl, $C_2$-$C_6$alkenylenearyl, $C_2$-$C_6$alkenyleneheteroaryl, $C_2$-$C_6$alkynyl, $C_2$-$C_6$alkynylene-aryl, $C_3$-$C_{12}$cycloalkenyl, heterocycloalkenyl, $C_1$-$C_6$alkylene-O—$C_1$-$C_6$alkyl, $C_1$-$C_6$alkylene-O—$C_3$-$C_{12}$cycloalkyl, $C_1$-$C_6$alkylene-O-heterocycloalkyl, $C_1$-$C_6$alkylene-O—$C_1$-$C_6$alkylene-$C_3$-$C_{12}$cycloalkyl and $C_1$-$C_6$alkylene-O—$C_1$-$C_6$alkylene-heterocycloalkyl, each $R_1$ group being optionally substituted with one or more independently-selected groups $R_5$;

$R_2$ and $R_3$ are each independently selected from the group consisting of hydrogen, halogen, $C_1$-$C_6$alkyl, $C_2$-$C_6$alkenyl, $C_2$-$C_6$alkynyl, $C_1$-$C_6$haloalkyl, $C_3$-$C_{12}$cycloalkyl, heterocycloalkyl, aryl and heteroaryl; or $R_2$ and $R_3$ connect to form, together with the carbon atom to which they are attached, a three to seven-membered carbocyclic or heterocyclic ring; and $R_4$ is selected from the group consisting of hydrogen, $C_1$-$C_6$alkyl, $C_2$-$C_6$alkenyl, $C_2$-$C_6$alkynyl, $C_1$-$C_6$haloalkyl, $C_3$-$C_{12}$cycloalkyl, heterocycloalkyl, aryl and heteroaryl;

X and Q are independently selected from $CH_2$, O, $NR_7$, S, SO and $SO_2$;

$R_5$ is selected from the group consisting of hydroxy, halogen, cyano, nitro, $CO_2R_6$, $CONHR_6$, $CON(R_6)_2$, $SO_2NHR_6$, $SO_2N(R_6)_2$, $C_1$-$C_6$alkyl, $C_1$-$C_6$alkoxy, $C_1$-$C_6$alkyl-ester, $C_1$-$C_6$alkyl-amide, $C_1$-$C_6$alkyl-acid, $C_1$-$C_6$haloalkyl, $C_6$haloalkoxy, $C_1$-$C_6$haloalkyl-ester, $C_3$-$C_{12}$cycloalkyl, heterocycloalkyl, aryl, heteroaryl, $C_1$-$C_6$hydroxyalkyl, $C_3$-$C_{12}$hydroxycycloalkyl, hydroxy-heterocycloalkyl, $C_1$-$C_6$cyanoalkyl, $C_2$-$C_6$alkenyl, $C_2$-$C_6$alkynyl, $C_3$-$C_{12}$cycloalkenyl, heterocycloalkenyl, $C_1$-$C_6$alkylenearyl, $C_1$-$C_6$alkyleneheteroaryl, $C_1$-$C_6$alkylene-O—$C_1$-$C_6$alkyl, $C_1$-$C_6$alkylene-O—$C_3$-$C_{12}$cycloalkyl, $C_1$-$C_6$alkylene-O-heterocycloalkyl, $C_1$-$C_6$alkylene-O—$C_1$-$C_6$alkylene-$C_3$-$C_{12}$cycloalkyl and $C_1$-$C_6$alkylene-O—$C_1$-$C_6$alkylene-heterocycloalkyl; and $R_6$ and $R_7$ are independently selected from the group consisting of hydrogen, $C_1$-$C_6$alkyl, $C_2$-$C_6$alkenyl, $C_2$-$C_6$alkynyl, $C_1$-$C_6$haloalkyl, $C_3$-$C_{12}$cycloalkyl, heterocycloalkyl, aryl and heteroaryl, provided that at least one of $R_1$, $R_2$ and $R_3$ comprises a fluorine atom.

In some embodiments, $R_1$ is selected from the group consisting of $C_1$-$C_6$alkyl, $C_1$-$C_6$cycloalkyl, heterocycloalkyl, aryl, heteroaryl, $C_1$-$C_6$alkylene-aryl, $C_1$-$C_6$alkylene-heteroaryl, $C_3$-$C_{12}$cycloalkenyl, heterocycloalkenyl, $C_1$-$C_6$alkylene-O—$C_3$-$C_{12}$cycloalkyl, $C_1$-$C_6$alkylene-O-heterocycloalkyl, $C_1$-$C_6$alkylene-O—$C_1$-$C_6$alkylene-$C_3$-$C_{12}$cycloalkyl and $C_1$-$C_6$alkylene-O—$C_1$-$C_6$alkylene-heterocycloalkyl, each $R_1$ group being optionally substituted with one or more independently-selected groups $R_5$, wherein $R_5$ is selected from the group consisting of hydroxy, halogen, cyano, nitro, $CO_2R_6$, $CONHR_6$, $CON(R_6)_2$, $SO_2NHR_6$, $SO_2N(R_6)_2$, $C_1$-$C_6$alkyl, $C_1$-$C_6$alkoxy, $C_6$haloalkyl, $C_1$-$C_6$haloalkoxy, $C_1$-$C_6$hydroxyalkyl, $C_1$-$C_6$cyanoalkyl, $C_2$-$C_6$alkenyl, $C_2$-$C_6$alkynyl and $C_1$-$C_6$alkylene-O—$C_1$-$C_6$alkyl.

In some embodiments, $R_1$ is selected from the group consisting of $C_1$-$C_6$cycloalkyl, heterocycloalkyl, aryl, heteroaryl, $C_1$-$C_6$alkylene-aryl, $C_6$alkylene-heteroaryl, each $R_1$ group being optionally substituted with one or more independently-selected groups $R_5$, wherein $R_5$ is selected from the group consisting of hydroxy, halogen, cyano, nitro, $C_1$-$C_6$alkyl, $C_1$-$C_6$alkoxy, $C_1$-$C_6$haloalkyl, $C_1$-$C_6$haloalkoxy, $C_1$-$C_6$hydroxyalkyl, $C_1$-$C_6$cyanoalkyl, and $C_1$-$C_6$alkylene-O—$C_1$-$C_6$alkyl.

In some embodiments, $R_1$ is selected from the group consisting of aryl, heteroaryl, $C_1$-$C_6$alkylene-aryl and $C_1$-$C_6$alkylene-heteroaryl, each $R_1$ group being optionally substituted with one or three independently-selected groups $R_5$, wherein $R_5$ is selected from the group consisting of hydroxy, halogen, cyano, nitro, $C_1$-$C_6$alkyl, $C_1$-$C_6$alkoxy, $C_1$-$C_6$haloalkyl, $C_1$-$C_6$haloalkoxy, $C_1$-$C_6$hydroxyalkyl, $C_1$-$C_6$cyanoalkyl, and $C_1$-$C_6$alkylene-O—$C_1$-$C_6$alkyl.

In some embodiments, $R_1$ is selected from the group consisting of $C_1$-$C_6$alkylene-aryl and $C_1$-$C_6$alkylene-heteroaryl, each $R_1$ group being optionally substituted with one or three independently-selected groups $R_5$, wherein $R_5$ is selected from the group consisting of hydroxy, halogen, cyano, nitro, $C_1$-$C_4$alkyl, $C_1$-$C_4$alkoxy, $C_1$-$C_4$haloalkyl, $C_1$-$C_4$haloalkoxy, $C_1$-$C_4$hydroxyalkyl, $C_1$-$C_4$cyanoalkyl, and $C_1$-$C_4$alkylene-O—$C_1$-$C_4$alkyl.

In some embodiments, $R_1$ is selected from the group consisting of $C_1$-$C_4$alkylene-aryl and $C_1$-$C_4$alkylene-heteroaryl, each $R_1$ group being optionally substituted with one or three independently-selected groups $R_5$, wherein $R_5$ is selected from the group consisting of hydroxy, Cl, F, cyano, nitro, $C_1$-$C_4$alkyl, $C_1$-$C_4$alkoxy, $C_1$-$C_4$fluoroalkyl, $C_1$-$C_4$fluoroalkoxy, $C_1$-$C_4$hydroxyalkyl, $C_1$-$C_4$cyanoalkyl, and $C_1$-$C_4$alkylene-O—$C_1$-$C_4$alkyl.

In some embodiments, $R_1$ is $C_1$-$C_4$alkylene-aryl optionally substituted with one $R_5$ group, wherein $R_5$ is selected from the group consisting of Cl, F, $C_1$-$C_4$alkyl, $C_1$-$C_4$alkoxy, $C_1$-$C_4$fluoroalkyl and $C_1$-$C_4$fluoroalkoxy.

In some embodiments, $R_1$ is $C_1$-$C_2$alkylene-phenyl substituted with one $R_5$ group, wherein $R_5$ is selected from the group consisting of Cl, F, $CH_3$, $CH_3O$, $CF_3$, $CF_2H$, $CF_3O$ and $CHF_2O$. In some embodiments, the $R_5$ group is located at the para position.

In some embodiments, $R_1$ comprises a difluoromethoxy or a trifluoromethoxy substituent. In some embodiments, $R_1$ is p-trifluoromethoxybenzyl. In some embodiments, $R_1$ is p-difluoromethoxybenzyl. In some embodiments, at least one of $R_2$ and $R_3$ is F and the other of $R_2$ and $R_3$ is H. In some embodiments, $R_2$ and $R_3$ are both F. In some embodiments, $R_1$ is p-trifluoromethoxybenzyl or p-difluoromethoxybenzyl and at least one of $R_2$ and $R_3$ is F and the other of $R_2$ and $R_3$ is H or $R_2$ and $R_3$ are both F.

In some embodiments, $R_2$ and $R_3$ are each independently selected from the group consisting of hydrogen, halogen, $C_1$-$C_6$alkyl and $C_1$-$C_6$haloalkyl. In some embodiments, $R_2$ and $R_3$ are each independently selected from the group consisting of hydrogen, Cl, F, $C_1$-$C_4$alkyl and $C_1$-$C_4$haloalkyl. In some embodiments, $R_2$ and $R_3$ are each independently selected from the group consisting of hydrogen, F, $CH_3$, $CF_3$ and $CF_2H$. In some embodiments, $R_2$ and $R_3$ are both H or are both F, or one of $R_2$ and $R_3$ is H and the other is F.

In some embodiments, $R_4$ is selected from the group consisting of hydrogen $C_1$-$C_4$alkyl and $C_1$-$C_4$haloalkyl. In some embodiments, $R_4$ is selected from the group consisting of hydrogen, $C_1$-$C_4$alkyl and $C_1$-$C_4$haloalkyl. In some embodiments, $R_4$ is selected from the group consisting of hydrogen and $CH_3$. In some embodiments, $R_4$ is H.

In some embodiments, X and Q are independently selected from O and $NR_7$, wherein $R_7$ is selected from the group consisting of hydrogen, $C_1$-$C_4$alkyl and $C_1$-$C_4$haloalkyl. In some embodiments, X and Q are independently selected from O and $NR_7$, wherein $R_7$ is selected from the group consisting of hydrogen and $CH_3$. In some embodiments, X is O. In some embodiments Q is selected from O and $NR_7$. In some embodiments Q is O.

In some embodiments, $R_6$ is selected from the group consisting of hydrogen and $C_1$-$C_4$alkyl.

Representative compounds according to the current application include, but not limited to the following examples:
7-Benzyloxy-4H benzo[1,4]oxazin-3-one;
7-(4-Fluoro-benzyloxy)-4H-benzo[1,4]oxazin-3-one;
7-(4-Difluoromethoxy-benzyloxy)-4H-benzo[1,4]oxazin-3-one;
7-(4-Trifluoromethoxy-benzyloxy)-4H-benzo[1,4]oxazin-3-one; and
7-Benzyloxy-2,2-difluoro-4H-benzo[1,4]oxazin-3-one; or a pharmaceutically-acceptable salt, solvate, tautomer, optical isomer, or combination thereof.

In some embodiments, the present application includes a compound having the formula:

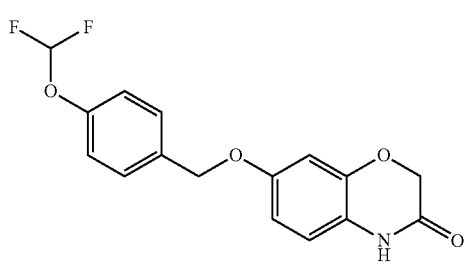

or a pharmaceutically-acceptable solvate or tautomer, or combination thereof.

It will be understood by those of skill in the art that when compounds of the present application contain one or more chiral centers, the compounds of the application may exist in, and be isolated as, enantiomeric or diastereomeric forms, or as a racemic mixture. The present application includes any possible enantiomers, diastereomers, racemates or mixtures thereof, of a compound of Formula (I). The optically active forms of the compound of the application may be prepared, for example, by chiral chromatographic separation of a racemate or chemical or enzymatic resolution methodology, by synthesis from optically active starting materials or by asymmetric synthesis based on the procedures described hereinafter. Resolution of the final product, an intermediate, or a starting material may be affected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

It will also be understood by those of skill in the art that certain compounds of the present application may exist in solvated, for example hydrated, as well as unsolvated forms. It will further be understood that the present application encompasses all such solvated forms of the compounds of Formula (I).

Within the scope of the application are also salts of the compounds of Formula (I). Generally, pharmaceutically acceptable salts of compounds of the present application are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present application having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine)

in an aqueous medium, followed by conventional purification techniques. Additionally, quaternary ammonium salts can be prepared by the addition of alkylating agents, for example, to neutral amines.

The compounds of Formulas (I) may crystallize in more than one form, a characteristic known as polymorphism, and such polymorphic forms ("polymorphs") are within the scope of Formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. Certain of the compounds described herein contain one or more chiral centers, or may otherwise be capable of existing as multiple stereoisomers. The scope of the present application includes mixtures of stereoisomers as well as purified enantiomers or enantiomerically/diastereomerically enriched mixtures. Also included within the scope of the application are the individual isomers of the compounds represented by Formula (I), as well as any wholly or partially equilibrated mixtures thereof. The present application also includes the individual isomers of the compounds represented by the formulas above as mixtures with isomers thereof in which one or more chiral centers are inverted.

The compounds of the application may be used in their labelled or unlabelled form. In the context of this application the labelled compound has one or more atoms replaced by an atom having an atomic mass or mass number different from the atomic mass or mass number usually found in nature. The labelling will allow easy quantitative detection of said compound.

In another embodiment of the compounds of the present application may be useful as diagnostic tools, radio tracers, or monitoring agents in various diagnostic methods, and for in vivo receptor imaging. The labelled isomer of the application preferably contains at least one radionuclide as a label. Positron emitting radionuclides are all candidates for usage. In the context of this application the radionuclide is preferably selected from $^2$H (deuterium), $^3$H (tritium), $^{11}$C, $^{13}$C, $^{14}$C, $^{131}$I, $^{125}$I, $^{123}$I, and $^{18}$F. The physical method for detecting the labelled isomer of the present application may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

In yet another one embodiment of the present application, the compound of Formula (I) may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

In yet another aspect, there is provided a pharmaceutical composition comprising a compound of Formula (I) and at least one pharmaceutically acceptable carrier and/or excipient. In a further aspect, the carrier is a pharmaceutically-acceptable carrier.

In another aspect, there is provided a pharmaceutical composition comprising therapeutically effective amount of a compound of Formula (I) to treat medical conditions such as epilepsy, neuropathic pain, acute and chronic inflammatory pain, migraine, tardive dyskinesia, anxiety and other related CNS disorders; such compositions can comprise a compound of Formula (I) in association with one or more pharmaceutically acceptable diluents, excipients and/or inert carriers.

For pharmaceutical use, the compounds of the present application are, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intra-arterially, intravenously or intrathecally. Administration can be by means of a pump for periodic or continuous delivery. The compounds of the application are administered alone, or are combined with a pharmaceutically-acceptable carrier or excipient according to standard pharmaceutical practice. For the oral mode of administration, the compounds of the application are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the application are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as ascorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, and mixtures of polyethylene glycols of various molecular weight and fatty acid esters of polyethylene glycol. For example, see Remington's Pharmaceutical Sciences, 16th Ed. (Mack Publishing, Easton, Pa., 1980, pp. 1530-1533) for further discussion of suppository dosage forms. Analogous gels or creams can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use in the present application include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use in the present application include those derived from non-toxic metals such as sodium or potassium, ammonium salts and organoamino salts such as triethylamine salts. Numerous appropriate such salts will be known to those of ordinary skill.

III. Methods of Use of the Application

In yet another aspect there is provided a method for treating at least one of epilepsy, neuropathic pain, acute and chronic inflammatory pain, migraine, tardive dyskinesia, anxiety and other related CNS disorders in a mammal, comprising administering to the mammal a therapeutically effective amount of a compound or composition noted above. In a further aspect, the mammal is a human. In still a further aspect, the compound or composition is administered orally and/or parenterally. In yet another aspect, the compound or composition is administered intravenously and/or intraperitoneally.

In yet a further aspect, there is provided the use of the compound or composition noted above for manufacture of a medicament for treatment of at least one of epilepsy, neuropathic pain, acute and chronic inflammatory pain, migraine, tardive dyskinesia, anxiety and other related CNS disorders. In yet a further aspect, there is provided the use of the compound or composition noted above for treatment of at least one of epilepsy, neuropathic pain, acute and chronic inflammatory pain, migraine, tardive dyskinesia, anxiety and other related CNS disorders in a mammal. In a further aspect, the mammal is a human. In still a further aspect, the compound or composition is administrable orally and/or parenterally. In yet another aspect, the compound or composition is administrable intravenously and/or intraperitoneally.

In some embodiments, the CNS diseases, conditions or disorders, include, but not limited to, epilepsy, epileptogenesis, convulsions, seizure disorders, tremor, essential tremor, myoclonus, anxiety, Parkinson's disease, Huntington's disease, Amyotrophic Lateral Sclerosis, Gilles de la Tourette's syndrome, depression, mania, manic depression, psychosis, schizophrenia, obsessive compulsive disorders (OCD), panic disorders, an eating disorder including anorexia nervosa, bulimia and obesity, narcolepsy, nociception, AIDS-dementia, senile dementia, peripheral neuropathy, autism, dyslexia, tardive dyskinesia, hyperkinesia, post-traumatic syndrome, social phobia, a sleeping disorder, pseudo dementia, Ganser's syndrome, pre-menstrual syndrome, late luteal phase syndrome, chronic fatigue syndrome, mutism, trichotillomania, jet-lag, hypertension, cardiac arrhythmias, a smooth muscle contraction disorder including convulsive disorders, angina pectoris, premature labor, convulsions, diarrhea, asthma, premature ejaculation and erectile difficulty, an endocrine system disorder including thyrotoxicosis and pheochromocytoma, a neurodegenerative disorder, including transient anoxia and induced neuro-degeneration, pain, mild, moderate or severe pain, acute pain, chronic pain, pain of recurrent character, neuropathic pain, pain caused by migraine, postoperative pain, phantom limb pain, neuropathic pain, chronic headache, central pain, pain related to diabetic neuropathy, to post-therpetic neuralgia or to peripheral nerve injury and an inflammatory disorder.

In a further aspect, the compounds of the present application may be useful as diagnostic tools or monitoring agents in various diagnostic methods, and in particular for in vivo receptor imaging (neuroimaging), and they may be used in labelled or unlabelled form. In some embodiments the disease, disorder or condition contemplated according to the application is selected from epilepsy, epileptogenesis, convulsions, seizure disorders, tremor, essential tremor, myoclonus, anxiety, Parkinson's disease, tardive dyskinesia and hyperkinesia. In some embodiments, the disease, disorder or condition is epilepsy, epileptogenesis, convulsions or seizure disorders.

In some further embodiments, the disease, disorder or condition is pain, including mild, moderate or even severe pain of acute, chronic or recurrent character, as well as pain caused by migraine, postoperative pain, or phantom limb pain. The pain may in particular be neuropathic pain, chronic headache, central pain, pain related to diabetic neuropathy, to post-herpetic neuralgia, or to peripheral nerve injury. Finally the compounds of the application may be useful for the treatment of withdrawal symptoms caused by termination of use of addictive substances. Such addictive substances include nicotine containing products such as tobacco, opioids such as heroin, cocaine or morphine, benzodiazepines and benzodiazepine-like drugs, and alcohol. Withdrawal from addictive substances is in general a traumatic experience characterized by anxiety and frustration, anger, anxiety, difficulties in concentrating, restlessness, decreased heart rate and/or increased appetite and/or weight gain.

The physician or other health care professional can select the appropriate dose and treatment regimen based on, for example, the subject's weight, age, and physical condition. Dosages will generally be selected to maintain a serum level of compounds of the application between about 0.01 μg/cc and about 1000 μg/cc, or between about 0.1 μg/cc and about 100 μg/cc. For parenteral administration, an alternative measure of dosage amount is from about 0.001 mg/kg to about 10 mg/kg (alternatively, from about 0.01 mg/kg to about 10 mg/kg), or from about 0.01 mg/kg to about 1 mg/kg (from about 0.1 mg/kg to about 1 mg/kg). For oral administrations, an alternative measure of the administration amount is from about 0.001 mg/kg to about 10 mg/kg (from about 0.1 mg/kg to about 10 mg/kg), or from about 0.01 mg/kg to about 1 mg/kg (from about 0.1 mg/kg to about 1 mg/kg). For administrations in suppository form, an alternative measure of the administration amount is from about 0.1 mg/kg to about 10 mg/kg, or from about 0.1 mg/kg to about 1 mg/kg.

IV. Methods of Preparation of the Compounds of the Application

The application additionally provides a process for the preparation of compounds of Formula (I). General and specific processes are discussed in more detail set forth in the Examples below.

The compounds of this application may be made by a variety of methods, including well-known standard synthetic methods. Illustrative general synthetic methods are set out below and then specific compounds of the application are prepared in the working Examples.

In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) Protecting Groups in Organic Synthesis, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of Formula (I).

Compounds of the present application can be prepared by various synthetic processes. The selection of a particular process to prepare a given compound of Formula (I) is within the purview of the person of skill in the art. The choice of particular structural features and/or substituents may therefore influence the selection of one process over another.

Some starting materials for preparing compounds of the present application are available from commercial chemical sources. Other starting compounds, as described below, are readily prepared from available precursors using straightforward transformations that are well known in the art.

Within these general guidelines, the compounds of Formula (I) generally can be prepared according to the methods illustrated in Schemes I to III. Variables in these methods are as defined for Formula (I) herein above unless otherwise specified.

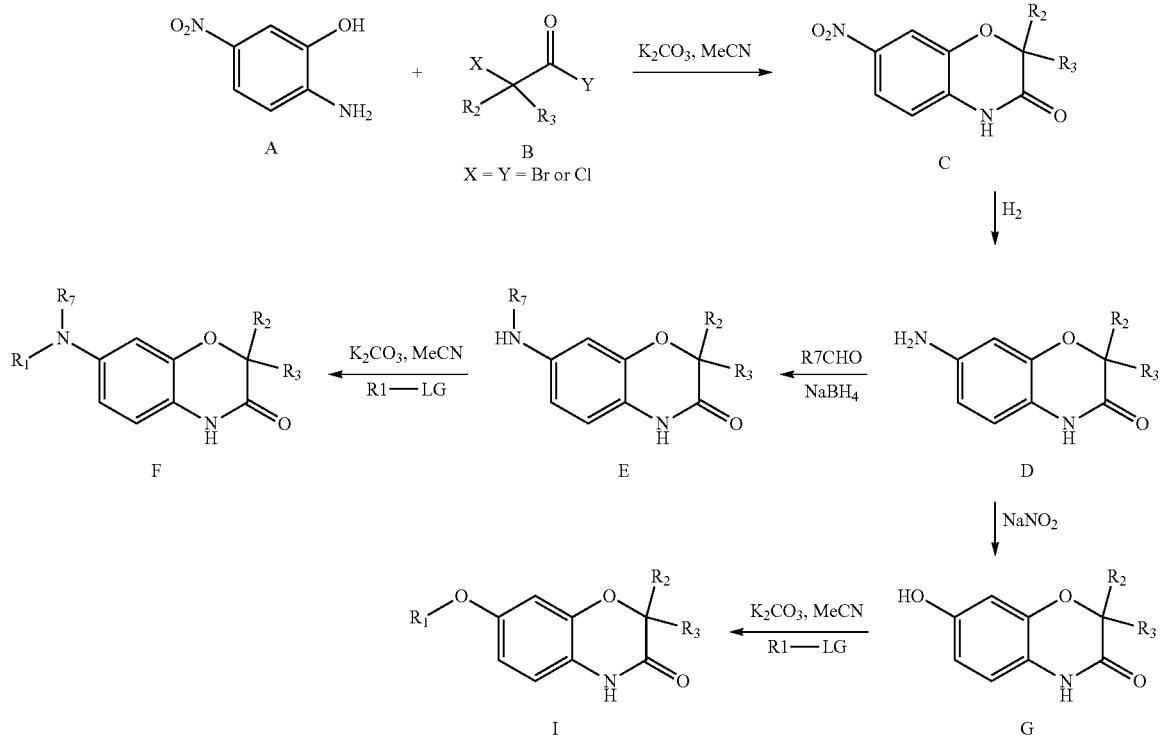

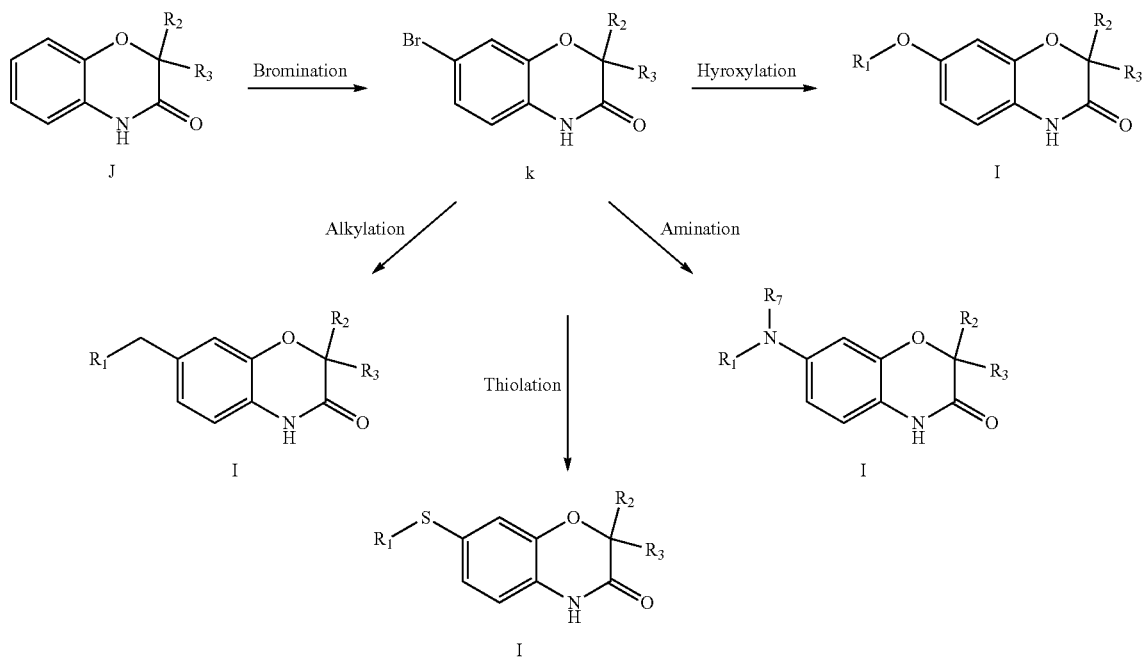

Scheme III

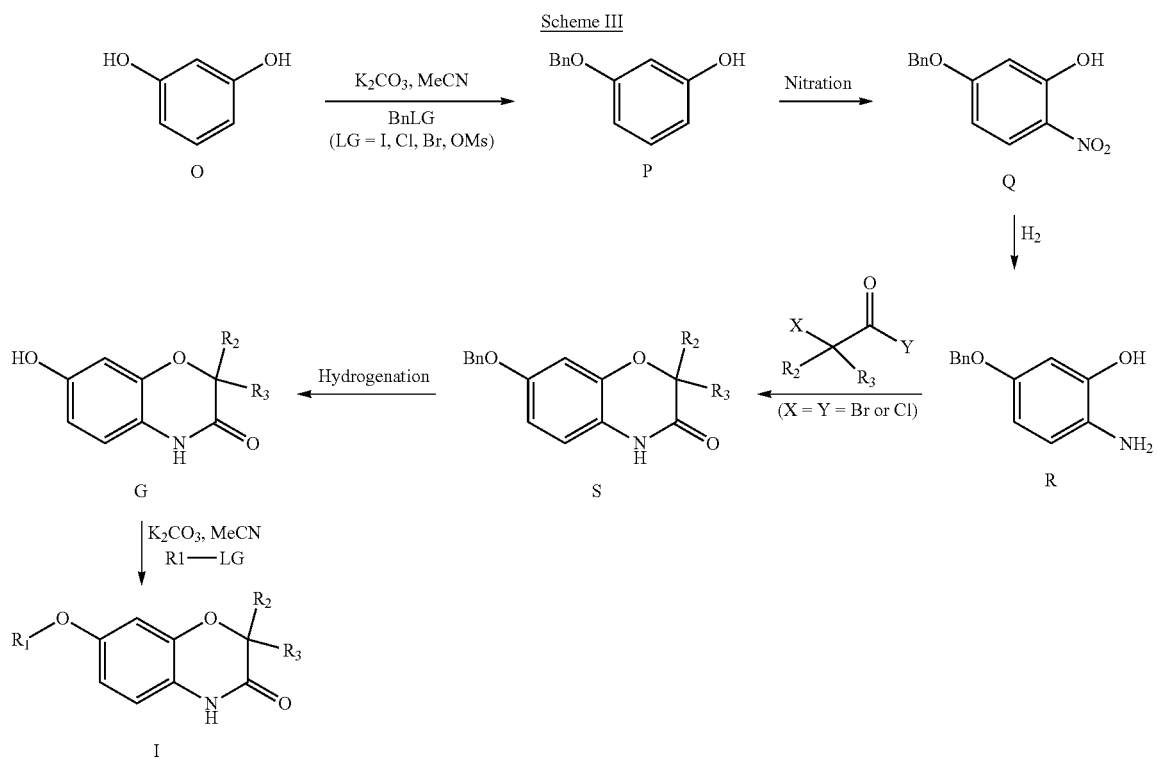

The compounds of this application wherein $R_1$, $R_2$ and $R_3$ are as defined above and Q is O or $NR_7$ wherein $R_7$ is as defined above can be prepared, for example, according to Scheme I. The benzoxazine-based intermediate (C) can be synthesized in a straightforward process from the commercially available 2-amino-5-nitro-phenol (A) by a condensation reaction of a halo-acetyl chloride, a non-limiting example is chloro-acetyl chloride (B) in the presence of a base, a non-limiting example of which is potassium or cesium carbonate in a polar solvent, non-limiting examples are acetonitrile and dimethyl-formamide to afford the corresponding to the 7-nitro-4H-benzo[1,4]oxazin-3-one intermediates (C), hydrogenation, non-limiting examples of which are catalytic hydrogenation and iron powder, of the nitro group yields 7-amino-4H-benzo[1,4]oxazin-3-one derivatives (D). Subsequent reductive-amination reaction with an appropriate aldehydes leads to the secondary amine intermediates (E), that are subsequently reacted with an halide, a non-limiting examples of which are substituted benzyl-chloride or bromide in the presence of a base, a non-limiting example of which is potassium or cesium carbonate in a polar solvent, non-limiting examples are acetonitrile, dimethyl-formamide and ethanol, to provide the targeted compounds (F). On the other hand, the amino functionality of 7-amino-4H-benzo[1,4]oxazin-3-one (D) is transformed to the key intermediate 7-hydroxy-4H-benzo[1, 4]oxazin-3-onehydoxy intermediates (G) using sodium nitrite in the presence of acid, a non-limiting example of which is sulfuric acid. Subsequent alkylation with $R_1$-LG (LG is a leaving group, a non-limiting examples of which is bromo, iodo or chloro) leads to the final compounds (I) (Pico Z T. et al., *Eur. J. Med. Chem.*, 2008, 43, 1216-1221).

Alternatively, the compounds of the application wherein $R_1$, $R_2$ and $R_3$ are as defined above and X is C, O, S or $NR_7$ wherein $R_7$ is as defined above can be prepared according to Scheme II. Regio-selective halogenations of benzo[1,4]oxazin-3-one derivatives (J) with halogen, non-limiting examples of which are bromine, iodine and chlorine in acidic reaction conditions, a non-limiting example of which is glacial acetic acid in the presence of a non-polar solvent, a non-limiting example of which is chloroform provides the 7-halo-4H-1,4-benzoxazin-3-one intermediates (K) (Hanson J R et al., *J. Chem. Research*, 2003, 1120-1128) that were used for the coupling reactions to form compounds with X is an oxygen (I), (Boyan X. et al., *Chem. Let.,* 2008, 37(2), 202-203; Nam T. et al., *Synthesis,* 2005, 9, 1397-1404; Hyun K. et al., *Org. Let.,* 2011, 13(9), 2368-2371, Rajesh P., *Synthesis,* 2010, (24), 4268-4272; Chuan T., Chinese *Chem. Lett.* 2009, 20(10), 1170-1174), compounds with X is a carbon (I) (Martinez, G. et al. *J. Med. Chem.,* 1992, 35(4), 620-628; Lemhadri M. et al., *Synthesis,* 2009, 6, 1021-1035; Alacid E, et al., *Eur. J. Org. Chem.* 2008, 18, 3102-3106; Bing M. et al., *Tetrahedron* 2007, 63(46), 11475-11488), compounds with X is a nitrogen (N) (Xiaolin L. et al., 2010, *Faming Zhuanli Shenqing,* 101863860; Qilong S. et al., 2008, *J. Am. Chem. Soc.,* 130(20), 6586-6596; Jadhav, V H. et al., *Cat. Comm.,* 2006, 8(1), 65-68), and compounds with X is a sulfur (I) (Chad E C. et al., *J. Org. Chem.,* 74(10), 4005-4008; 2009; Keniley L. et al., *Inorg. Chem.* 2010 (Washington, D.C., United States), 49(4), 1307-1309; Sakaki S. et al., *Bioorg. Med. Chem. Lett.,* 2007, 17(17), 4804-4807).

Alternatively, the compounds of this application wherein $R_1$, $R_2$ and $R_3$ are as defined above and Q is oxygen may be prepared according to Scheme III. Mono-protection of commercially available resorcinol (O), a non-limiting example of which is benzylation to provide 3-benzyloxyphenol (P), which is subjected to nitration conditions to yield (Q), and subsequent nitro group reduction leads to the 2-amino-5-benzyloxy-phenol intermediate (R) (Ming X. et al., *Chinese*

Chem. Lett., 2007, 18(8), 905-908; Maleski, R J. et al. *Synth. Commun.*, 1995, 25(15), 2327-35). Intermediate (R) is transformed to (I) in a similar manner as described in Scheme I.

The above disclosure generally describes the present application. A more complete understanding can be obtained by reference to the following specific Examples. These Examples are described solely for purposes of illustration and are not intended to limit the scope of the application. Changes in form and substitution of equivalents are contemplated as circumstances may suggest or render expedient. Although specific terms have been employed herein, such terms are intended in a descriptive sense and not for purposes of limitation.

EXAMPLES

Abbreviations atm Atmosphere
aq. Aqueous
BINAP 2,2'-bis(diphenylphosphino)-1,1'-binaphthyl
Boc tert-butoxycarbonyl
DCM Dichloromethane
DEA N,N-Diisopropyl ethylamine
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
Et$_2$O Diethylether
EtOAc Ethyl acetate
EtOH Ethanol
EtI Iodoethane
Et Ethyl
Fmoc 9-fluorenylmethyloxycarbonyl
hr(s) hour(s)
mins minutes
HetAr Heteroaryl
HPLC High performance liquid chromatography
LAH Lithium aluminium hydride
LCMS HPLC mass spec
MCPBA m-Chlorbenzoic acid
MeCN Acetonitrile
MeOH Methanol
Min Minutes
MeI Iodomethane
Me Methyl
n-BuLi 1-Butyllithium
NaOAc Sodium acetate
NaOH Sodium hydroxide
NaH Sodium hydrade
NMR Nuclear magnetic resonance
NMP N-Methyl pyrrolidinone
NMM N-Methyl morpholine
ON Over Night
RT Room Temperature
TEA Triethylamine
THF Tetrahydrofurane
OMs Mesylate or methane sulfonate ester
OTs Tosylate, toluene sulfonate or 4-methylbenzene sulfonate ester
PCC Pyridinium chlorochromate
PPTS Pyridinium p-toluenesulfonate
TBAF Tetrabutylammonium fluoride
pTsOH p-Toluenesulfonic acid
SPE Solid phase extraction (usually containing silica gel for mini-chromatography)
sat. Saturated
Gp Protecting group
LG Leaving group Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiple), or b (broad).

Example 1: Representative Synthesis of Exemplary Compounds of the Application Exemplary compounds I(A) to I(E) of the present application are as illustrated in the following Table 1, their pharmaceutically acceptable salts, hydrates, solvates, optical isomers, and combinations thereof:

TABLE 1

| Compound # | Chemical Structure | Nomenclature |
| --- | --- | --- |
| 1 (Comparative example) | 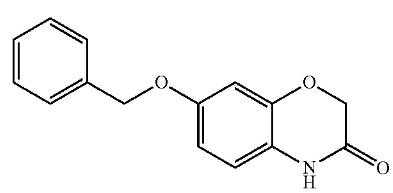 [SMILES: O=C1COc2cc(OCc3ccccc3)ccc2N1] | 7-Benzyloxy-4H benzo[1,4]oxazin-3-one |
| I(A) | 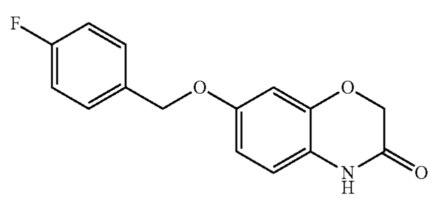 [SMILES: O=C1COc2cc(OCc3ccc(F)cc3)ccc2N1] | 7-(4-Fluoro-benzyloxy)-4H-benzo[1,4]oxazin-3-one |

TABLE 1-continued

| Compound # | Chemical Structure | Nomenclature |
|---|---|---|
| I(B) | 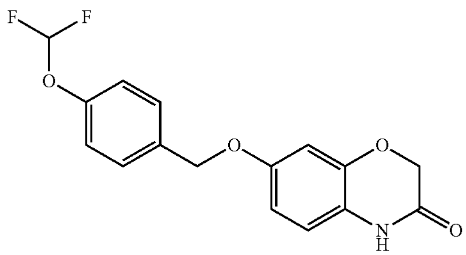 [SMILES: O=C1COc2cc(OCc3ccc(OC(F)F)cc3)ccc2N1] | (7-(4-Difluoromethoxy-benzyloxy)-4H-benzo[1,4]oxazin-3-one |
| I(C) | 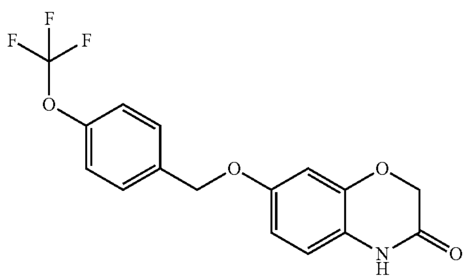 [SMILES: O=C1COc2cc(OCc3ccc(OC(F)(F)F)cc3)ccc2N1] | 7-(4-Trifluoromethoxy-benzyloxy)-4H-benzo[1,4]oxazin-3-one |
| I(D) | 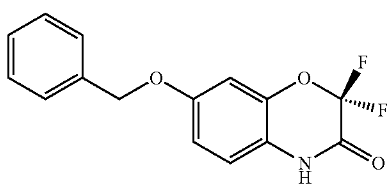 | 7-Benzyloxy-2,2-difluoro-4H-benzo[1,4]oxazin-3-one |

Preparation of 7-Benzyloxy-4H benzo[1,4]oxazin-3-one (Compound 1)—Comparative Example

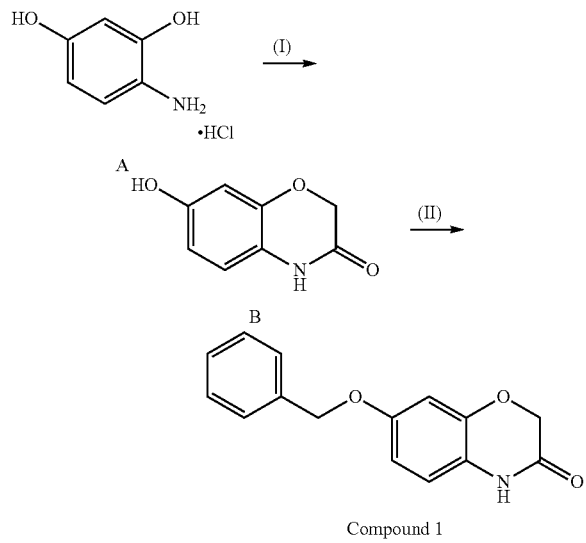

Compound 1

Step. 1: 7-Hydroxy-4H-benzo[1,4]oxazin-3-one (B)

Method (1):

$K_2CO_3$ (30.6 g, 221.4 mmol, 4 eq) was dissolved in water (120 mL) in a 250 mL round bottomed flask, vacuum degassed 3 times, then cooled to 0° to 5° C. 4-Amino resorcinol HCl (A) (9 g, 55.69 mmol, 1 eq) was added through a strong nitrogen purge, and the blue solution was again degassed 3 times. Choro-acetyl chloride (5.4 mL, 69.61 mmol, 1.25 eq) was dissolved in toluene (27 mL), and was added over 30 min maintaining the temperature below 5° C. The ice bath was removed, and the mixture (biphasic with suspended crystalline product) was stirred overnight. 7-Hydroxy-4H-benzo[1,4]oxazin-3-one (B) was then isolated via filtration giving 7.6 g, 83.5%) after a water wash (2×200 mL) and drying; HRMS [M+H] calcd, 166.04987; found, 166.04929.

Method (2):

To a solution of 4-aminoresorcinol hydrochloride (A) (5.0 g, 30.94 mmol) in acetonitrile (100 mL) at 0° C. was added cesium carbonate (30.2 g, 92.80 mmol) followed by a dropwise addition of chloroacetyl chloride (2.6 mL, 32.49 mmol). The reaction mixture was stirred at room temperature for overnight and then was diluted with absolute ethanol (100 mL). The insoluble materials were filtered and rinsed with 2× 50 mL of absolute ethanol. The filtrate was concentrated under vacuum to afford the crude product as a purple oily solid. The solid was dissolved in methanol (50 mL), silica was added, and the solvent was removed again under vacuum. The solid was loaded onto a pad of silica (800 mL) and eluted with 1:1 ethyl acetate in dichloromethane followed by 100% dichloromethane. After removal of the solvents, the product (B) was obtained as an orange solid (3 g, 60%).

Step. 2: 7-benzyloxy-4H-1,4-benzoxazin-3-one (Compound 1)

A mixture of the above 7-Hydroxy-4H-benzo[1,4]oxazin-3-one (B, 2.5 g 15.43 mmol) and bromomethyl-benzene (3.3 g 17.74 mmol) in 65 ml anhydrous ethanol was refluxed for 4 to 6 hours in the presence of $K_2CO_3$ (12.8 g, 92.6 mmol). After the solvent was removed, the residue was diluted with water (50 mL). The precipitate was filtered. The solid obtained was dissolved in EtOAc (50 mL), and washed with water and brine (2×50 mL). Dried over $MgSO_4$, concentrated led to the crude product, this was triturated with ether and filtered to get pure product (2 g). This process was repeated 3×) to provide a total of (3.2 g, 82%) of compound 1 as white light powder. $^1$H-NMR (300 MHz, $CDCl_3$): δ 8.16 (broad s, 1H), 7.40-7.31 (m, 5H) (s, 1H), 6.71 (s, 1H), 6.69-6.57 (m, 2H), 5.01 (s, 2H), 4.58 (s, 2H).

In a similar procedure the following compounds were synthesized as illustrated in the following Table 2:

Example 2: The Maximal Electroshock Seizure (MES) Rat Model (Epilepsy Indication)

Animals and Housing:

Male, Sprague-Dawley rats and CD-1 mice were used for all studies. All animals were allowed ad-lib access to food and water except during experiment. Animals were housed within an animal vivarium maintained under a 12 h light: dark cycle (lights on: 07:00 h), and all experiments were conducted in the animals light phase. For all experiments, animals were habituated to the vivarium for a minimum of 72 h before experimentation. The experimental procedures used in the present investigation were conducted under the

TABLE 2

| Compound # | Structure | Name | Yield |
|---|---|---|---|
| I(A) | 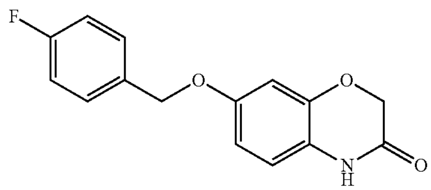 [SMILES: O=C1COc2cc(OCc3ccc(F)cc3)ccc2N1] | 7-(4-Fluoro-benzyloxy)-4H-benzo[1,4]oxazin-3-one | 0.99 g, (87%) |
| NMR | $^1$H-NMR (300 MHz, $CDCl_3$): δ 8.18 (broad s, 1H), 7.39-7.36 (m, 2H), 7.09-7.07 (m, 2H), 6.65 (dd, 1H), 6.56 (m, 2H), 4.97 (s, 2H), 4.59 (s, 2H). | | |
| I(B) | 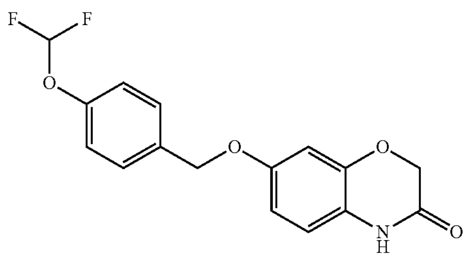 [SMILES: O=C1COc2cc(OCc3ccc(OC(F)F)cc3)ccc2N1] | (7-(4-Difluoromethoxy-benzyloxy)-4H benzo[1,4]oxazin-3-one | 2.18 g, (72%) |
| NMR | $^1$H-NMR (300 MHz, $CDCl_3$): δ 7.91 (broad s, 1H), 7.40 (d, 2H), 7.13 (d, 2H), 6.71-6.55 (m, 4H), 4.98 (s, 2H), 4.59 (s, 2H). | | |
| I(C) | 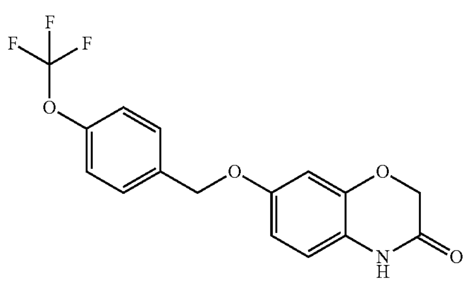 [SMILES: O=C1COc2cc(OCc3ccc(OC(F)(F)F)cc3)ccc2N1] | 7-(4-Trifluoromethoxy-benzyloxy)-4H-benzo[1,4]oxazin-3-one | 1.5 g, (83%) |
| NMR | $^1$H-NMR (300 MHz, $CDCl_3$): δ 8.16 (broad s, 1H), 7.64 (d, 2H), 7.55 (d, 2H), 6.73-6.70 (m, 1H), 6.63-5.55 (m, 2H), 5.07 (s, 2H), 4.59 (s, 2H). | | |
| I(D) | 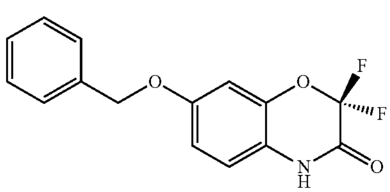 | 7-Benzyloxy-2,2-difluoro-4H-benzo[1,4]oxazin-3-one | 0.84 g, (50%) |
| NMR | $^1$H NMR (300 MHz, $CDCl_3$): δ (ppm) 8.19 (broad, 1H), 7.41-7.32 (m, 5H), 6.88-6.76 (3, mH), 5.04 (s, 2H). | | |

Association for Assessment and Accreditation of Laboratory Animal Care (AAALAC) and the Canadian Council on Animal Care (CCAC) guidelines.

All compounds were sonicated in 5% Tween 80® in saline or methylcellulose 0.5% (wgt/vol), using MC and sterile water and injected in a dose volume of 5 ml/kg or 10 ml/kg (rat), and 10 ml/kg (mouse). Drugs were administered by either the oral, intraperitoneal or intravenous route.

Male Sprague-Dawley rats of body weight 80-100 g were used for these studies. Each experiment was conducted over 3 consecutive days. On day 1 and 2, each rat received a single electrical stimulus (150 mA, 0.2 s duration, 60 Hz) via corneal electrodes moistened with saline (Shock stimulator type 221: Harvard apparatus). Only rats that displayed a full tonic extensor on day 1 and 2 were entered into the drug study conducted on day 3. Typically this reflected approximately 70-90% of the initial group. In this way, rats which did not produce a reliable tonic extensor to the MES stimulus were excluded from the experiment.

On the test day following a defined drug pretreatment period, rats received a maximal electroshock (150 mA, 0.2 s duration, 60 Hz) via corneal electrodes. Protection was defined as absence of a full tonic seizure within 10 s of stimulus delivery. Twenty minutes before the MES procedure, the animals were tested on a fixed speed rotorod (best score from 3 trials at 8 r.p.m, trial duration=60 s) to give an early assessment of drug effect on gross motor function.

Several exemplary compounds of the application were active in this assay, with $ED_{50}$ values of below 50 mg/kg in rat (po) as illustrated in the following Table 3:

TABLE 3

| Compound # | MES (po) $ED_{50}$ mg/kg, [4 hours] | Rotorod (po) $ED_{50}$ mg/kg, [4 hours] | PI |
|---|---|---|---|
| I(B) | 20.1 ± 0.7 | >500 | >25 |
| I(D) | 30.5 ± 0.8 | >120 | >3.9 |
| 1 | >300 | — | — |

Example 3: s.c Pentylenetetrazole (PTZ) Mouse Model (Epilepsy Indication)

Sixty minutes following drug or vehicle pretreatment, all mice received a single subcutaneous injection of pentylenetetrazol (PTZ; 85 mg/kg). The animals were then transferred to single observation cages (dimension: 11.5"×7.5"×5") and observed continuously for 30 min. Preliminary experiments established that at the 85 mg/kg s.c dose of PTZ, at least one single episode of clonic seizure was elicited in >95% of control animals. Protection was defined as complete absence of a clonic seizure over the 30 min observation period. In the event of a seizure, the onset latency from PTZ injection was recorded.

Several exemplary compounds of the application demonstrated anticonvulsant activity in this assay, with $ED_{50}$ values of below 300 mg/kg in mice (ip). Comparative compound 1 had $ED_{50}$ values of above 300 mg/kg in mice (ip).

Example 4: 6-Hz Psychomotor Seizure Mouse Model (Epilepsy Indication)

Sixty minutes following drug or vehicle pretreatment, all mice received an electrical stimulus (6 Hz, 0.2 ms pulse width, 3 s duration, 32 mA) via corneal electrodes moistened with saline (ECT unit 57800; Ugo Basile). Preliminary experiments established that these stimulus parameters elicited a psychomotor seizure, defined as the expression of at least one of the following behaviors: stun/immobility, forelimb clonus, straub tail, vibrissae tremor, lateral head movement in >95% of control animals. Protection was defined as complete absence of all the above behaviors within 20 s of stimulus delivery. The effective dose of compound necessary to protect against psychomotor seizures to 50% of controls (i.e. $ED_{50}$) was determined by curve fitting program (Prism v. 4.02).

Compound I(B) of the application demonstrated anticonvulsant activity in this assay, with $ED_{50}$ values of below 100 mg/kg in mice (ip) as illustrated in the following Table 4:

TABLE 4

| Compound # | 6 Hz (ip) $ED_{50}$ mg/kg, [0.5 hour] | Rotorod (ip) $ED_{50}$ mg/kg, [0.5 hours] | PI |
|---|---|---|---|
| I(B) | 17.4 ± 0.6 | >500 | >28 |

Example 4: Intravenous Metrazol Seizure Threshold Test (i.v. MET)

The iv-Met test provides a measure of a test substance's ability to raise or lower seizure threshold. Two doses of the test compound are usually employed in this test, the MES $ED_{50}$ and the $TD_{50}$ determined following ip quantification testing in mice. Randomly selected mice are injected intraperitoneally 2 minutes apart with either the vehicle or the two test drug doses, maintaining the same order of dosing until 30 mice have been injected. At the previously determined TPE, 0.5% heparinized Metrazol solution is infused at a constant rate of 0.34 ml/min into a lateral tail vein of an unrestrained mouse. Infusion is by means of a Sage syringe pump (model 341 A) and a 10 ml B-D plastic syringe connected to a length of No 20 P.E. tubing. A 27 gauge stainless steel needle with the hub removed is connected to the tubing and inserted into a vein, bevel side up and secured to the tail by a narrow piece of adhesive tape. For the placement of the needle, the mouse is restrained in a cone shaped device with only the tail exposed. The rate selector is set on 4, and the switch is set at ml/min. At the start of the infusion, a hemostat clamped to the tubing to prevent backflow is removed, the infusion started, and two stopwatches started. The time in seconds from the start of the infusion to the appearance of the "first twitch" and the onset of sustained clonus is recorded. The times to each endpoint are converted to mg/kg of Metrazol for each mouse as follows:

$$\text{mg/kg Met} = \frac{\text{Inf time }(T) \times \text{Rate of inf (mL/min)} \times \text{mg Met/mL} \times 1000 \text{ g}}{60 \text{ sec} \times \text{Weight }(W) \text{ of animal in g}}$$

$$= \frac{T \times 0.34 \times 5 \times 1000}{60 \times W} = \frac{28.33 \times T}{W} = \text{mg/kg of Metrazol}$$

The mean and standard error for each of the 3 groups and the significance of the difference between the test groups and the control are calculated. An increase in mg/kg to first twitch or to clonus indicates the test substance increases seizure threshold, whereas a decrease indicates that the test substance decreases seizure threshold and may be proconvulsant.

Exemplary compounds of the application were found to increases seizure threshold in this model. For example, compound I(B) dose-dependently increased the seizure threshold in this mouse Seizure model (FIG. 1).

Example 5: Frings Audiogenic Seizure (AGS)-Susceptible Mouse Model

Frings audiogenic seizure (AGS)-susceptible mice model examines the ability of an investigational drug to alter the onset and/or severity of seizures in a genetic mouse model of seizure susceptibility. Mice are genetically susceptible to sound-induced reflex seizures. Their seizure phenotype is characterized by wild running, loss of righting reflex, tonic flexion, and tonic extension in response to high-intensity sound stimulation. In contrast to other seizure models, the Frings AGS-susceptible mouse, like the DBA2J AGS-susceptible mouse, is non-discriminatory with respect to clinical categories of anticonvulsant drugs, and thus, does not offer high predictive value in screening investigational compounds. For example, the prototypical anticonvulsants phenytoin and ethosuximide display widely divergent clinical spectrums in humans, but are both active against sound-induced seizures in mice. Yet, the preclinical utility of this animal model rests in the useful information that can be obtained within a genetically susceptible model of seizures. Further, efficacy in this model provides proof of concept of brain bioavailability following systemic administration. The Frings AGS-susceptible mouse has a well-validated epilepsy phenotype that makes it particularly useful as a screening model. Beginning at about 21 days of age, Frings AGS-susceptible mice display prominent seizure activity in response to a high-intensity sound stimulus. They then remain susceptible to sound throughout their life. This is in stark contrast to the DBA2J AGS-susceptible mouse, which is the other common model of sound-induced seizures, as DBA2J mice are only susceptible to sound-induced seizures during a narrow developmental window (post-natal days 18-30). Thus, the Frings AGS-susceptible mouse seizures respond to a wide range of CNS-active drugs and display sound-induced seizures throughout their lifetime. In this regard, Frings AGS-susceptible mice are a highly useful screening model for the identification and characterization of compounds potentially effective against inherited epilepsy.

Methods:

Male and female Frings audiogenic seizure-susceptible mice (18-25 g) are maintained in an in-house colony at the University of Utah. For each screening test, groups of 8 mice each are treated i.p. with varying doses of the investigational compound. At the time of peak effect as determined in the MES test (Test 4 in CF1 mice), individual mice are placed in a round plexiglass jar (diameter, 15 cm, height, 18 cm) and exposed to a sound stimulus of 110 decibels (11 KHz) delivered for 20 sec. Mice are observed for 25 sec for the presence or absence of hind limb tonic extension. Mice not displaying hind limb tonic extension are considered protected. The severity of a seizure may also be quantitated by assigning a numerical score to the observed response, e.g. no response—0; wild running for <10 sec—1; wild running for >10 sec—2; clonic seizure—3; forelimb extension/hind limb flexion—4; tonic seizure—5.

Exemplary compounds of the application are effective in this mouse model. For example. compound I(B) dose-dependently blocks AGS in the Frings AGS-susceptible mouse model with an ED50 of 13.00±2.00 mg/kg and superior Protective index compared to antiepileptic drugs ($TD_{50}/ED_{50}$) of 77, see following Table 5):

TABLE 5

| Drug | $ED_{50}$ (mg/kg, i.p.) | P.I[a] $(TD_{50}/ED_{50})$[b] |
|---|---|---|
| Compound I(B) | 13.0 ± 2.0 | 77 |
| Carbamazepine | 11.2 | 4.1 |
| Ethosuximide | 328 | 1 |
| Felbamate | 10 | 22 |
| Gabapentin | 91.1 | >5.5 |
| Lamotrigine | 2.39 | 13 |
| Levetiracetam | NT | NT |
| Phenytoin | 3.8 | 11 |
| Valproic Acid | 155 | 2.6 |

[a]Protective index = $TD_{50}/ED_{50}$)
[b]Calculated with $TD_{50}$ in mice and $ED_{50}$ in Frings mice
NT: Not tested

Example 6: Hippocampal Kindled Rat Model (Focal Seizures)

Hippocampal Kindled Rat Test is designed to quantify the anticonvulsant effects of a test compound in the kindled rat model. Rats treated by i.p. injection.

The Kindled Rat is a model of temporal lobe epilepsy, which is the most common and drug-resistant type of adult focal epilepsy (Morimoto et al., 2004). In this model, repetitive electrical stimulation of the hippocampus causes progressively stronger seizure responses triggered by stimuli that initially did not elicit such responses. This acquired hyper-responsiveness is called kindling and results not only in increased seizure responses but also in an elongation of the after-discharge duration seen on an EEC recording. Electrodes are implanted into the hippocampus of anesthetized rats, which are then allowed to recover for one week. Following the rapid kindling protocol (Lothman and Williamson, *Brain Res* 1994, 649:71-84), the rats are stimulated with 200 jiA for 10 s, 50 Hz, every 30 minutes for six hours on alternate days until they are fully kindled (4-5 stimulus days). After one week of rest, the animals are given the same electrical stimulus which serves as a baseline. The animals are pretreated with the test compound (generally via i.p. injection) and then tested at various intervals. At each time point, the behavioral seizure score (BSS) and after-discharge duration (ADD) is recorded. The BSS's are scored according to the following criteria (Racine, *Electroencephalogr Clin Neurophysiol* 1972, 32:281-94): Stage 1—mouth and facial clonus; Stage 2—stage 1 plus head nodding; Stage 3—stage 2 plus forelimb clonus; Stage 4—stage 3 plus rearing; and Stage 5—stage 4 plus repeated rearing and falling.

The afterdischarge threshold (ADT) can also be measured in the kindled rat. The ADT is defined as the lowest current at which an afterdischarge of at least 4 s is elicited. On the day of the test the individual ADT of each rat is determined by increasing the current intensity in a stepwise fashion until the rat displays an electrographic afterdischarge with duration of at least 4 sec. The initial stimulation is conducted at an intensity of 20 uA with 10 uA increments every 1-2 min until an afterdischarge is elicited. Fifteen minutes after the pre-drug threshold determination, a single dose of the test substance is administered to two animals in a volume of 0.04 ml/10 g body weight. In this way the animals serves as its own control. The individual rat ADT is then determined at varying times (i.e., 0.25, 1, 2, and 4 hr) after drug administration.

Exemplary compounds of the application were effective in this model. For example, compound I(B) (<300 mg/kg i.p.) produced a dose related suppression of fully kindled (stage 5) seizures compared to vehicle controls.

Example 7: Amygdala Kindled Rat Model (Focal Seizures)

Amygdala kindling model is an animal model for complex partial seizures, which is the most common type of epilepsy in adults and is often drug resistant. Exemplary compounds of the application were effective in this model. For example, compound I(B) (<100 mg/kg i.p.) produced a dose related suppression of fully kindled (stage 5) seizures compared to vehicle controls.

Example 8: Corneal Kindling Mouse Model (Focal Seizures)

Mice are kindled electrically with 3 sec stimulation, 8 mA, 60 Hz, and coneal electrodes to a criterion of 10 consecutive Stage 5 seizures (facial clonus and head nodding progressing to forelimb clonus, and finally rearing and falling accompanied by a generalized clonic seizure as described by Racine (Racine R J. *Neurophysiol.*, 1972. 32: p. 281-294) Stage 5 is generally reached after twice daily stimulation for 8 days. With continued stimulation once a day, animals usually progress to a reproducible Stage 5 after 10-14 additional days. At least 72 hours after the mice have been kindled, the test substance is administered either i.p. or p.o. and, at the previously determined TPE, each animal is given the electrical stimulus indicated above. Following stimulation, the animals are observed for the presence or absence of the rearing and falling criteria of a Stage 5 seizure. Treated animals not displaying a Stage 3, 4, or 5 seizure are considered protected. The dose of the test substance is varied between the limits of 0 and 100% efficacy, and the ED50 and 95% confidence intervals calculated by probit analysis. Mean values and the S.E.M. are calculated for the length of clonus and seizure duration and p values are determined by the Student's t-test.

Exemplary compounds of the application were effective in this model. For example, compound I(B) produced a dose related suppression of fully kindled (stage 5) seizures compared to vehicle controls with $ED_{50}$=118.66±1.81 mg/kg (see following Table 6):

TABLE 6

| Dose (mg/kg) | N/F(1) | Individual Seizure Scores | Average Seizure |
|---|---|---|---|
| 35 | 0/8 | 5, 5, 5, 5, 5, 5, 5, 5 | 5 |
| 70 | 1/8 | 5, 5, 5, 5, 5, 5, 5, 2 | 4.6 |
| 140 | 5/8 | 0, 0, 5, 0, 1, 5, 5, 3 | 2.4 |
| 300 | 8/8 | 0, 0, 0, 3, 3, 0, 0, 0 | 0.8 |

(1)Number of animals active over the number tested

Example 9: Model of Mesial Temporal Lobe Epilepsy (mTLE), Mouse

The MTLE mouse model recapitulates many of the characteristics observed in human patients with temporal lobe epilepsy (TLE). The MTLE mouse is characterized by an initial neurotoxic event, a unilateral intrahippocampal injection of kainic acid (KA) into the dorsal hippocampus, which induces non-convulsive SE lasting several hours. This initial event is followed by a latent phase. Two to three weeks after KA injection, spontaneous recurrent hippocampal paroxysmal discharges (HPD) are only recorded in the epileptic hippocampus and remain stable and stereotyped for the whole life of the animal. These HPDs occur spontaneously about 30-60 times per hour when the animals are in a state of quiet wakefulness, generally last 15-20 sec and are associated with behavioral arrest and/or mild motor automatisms. Adult, male 057/B16 mice are stereotaxically injected with kainate (1 nmol in 100 nL) and implanted with 1 bipolar electrode in the dorsal hippocampus, and then allowed to recover for four weeks prior to evaluation in the screening protocol. Using a group size of 4 MTLE mice per dose of investigational compound, the compounds are typically first tested using the 6 Hz 44 mA ED50 value. If a compound demonstrates efficacy at this dose, the dose can then be increased depending on other relevant factors; i.e., the known TD50, to vary the protection observed. For all acute studies, drug conditions are counter-balanced in MTLE mice over a two week period using a Latin square dosing protocol. Animals are used as their own controls. Digital EEG recordings are performed on freely moving animals for 20 minutes pre-injection (reference period) and 90 minutes post-injection. Data are analyzed for the period of 10 minutes before and 10 minutes after peak time of effect of the investigational compound, as determined from the 6 Hz 44 mA seizure test. The effects of the injected compound are compared to the reference period. Any accompanying effect on animal behavior is noted. Data are presented as the raw number of HPDs during the analyzed 20 min period (10 minutes before and 10 minutes after peak time of effect of compound) for each MTLE mouse, group mean number of HPDs, and effect on suppression as represented by percent of baseline HPD values.

Exemplary compounds of the application were effective in this model. For example, at a dose of 125 mg/kg compound I(B) was found to be effective against spontaneous recurrent hippocampal paroxysmal discharges (HPD) in mice previously lesioned with a unilateral intrahippocampal injection of kainic acid (KA) (see following Table 7 and FIG. 1).

TABLE 7

Table 7: Effect of Example I(B) (80-160 mg/kg) vs. keppra (600 mg/kg) on Hippocampal Paroxysmal Discharges (HPD) in Mice 4 Weeks after Unilateral Intra-hippocampal KA Injection.

| Compound | Dose (mg/kg) | Mean HPD Counts | Effect (% baseline) | SEM (% of baseline) |
|---|---|---|---|---|
| I(B) | 160 | 23.8 | 100 | 11.4 |
|  |  | 4.25 | 17.9 |  |
| I(B) | 80 | 17.3 | 100 | 15.0 |
|  |  | 7.25 | 42.0 |  |
| Levetiracetam (Keppra) | 600 | 20.8 | 100 | 16.2 |
|  |  | 14.3 | 68.7 |  |

Example 10: Mouse Formalin Test (Pain Indication)

The formalin test is performed according to the method of Tjolsen et al. Pain, 1992. 51(1). An injection of 0.5% formalin (Sigma) is made into the planter region of the right hind paw of an adult (26-30 g) male CF-1 mouse. Subdermal formalin injection elicits a distinct behavioral profile characterized by the mouse licking the affected paw. The behavior is characteristically biphasic in nature. For example, immediately following the injection the mouse licks the paw intensely for approximately 10 min. This is referred to as phase 1 (or, the acute phase) and is followed by a brief latent period (<5 minutes) where there is little behavioral activity. A more prolonged period of about 20-30 min of activity then ensues, which constitutes phase 2 (or, the inflammatory phase). Prior to the administration of the investigational drug or vehicle, each mouse undergoes a 15-min conditioning period in one of several 6" tall plexiglass tubes (4" diameter) that are placed in front of a mirror. It is in these tubes that mice are later observed for the licking activity for the duration of the experiment. Following the conditioning, the test substance is administered i.p. in a dose equivalent to the MES ED50 and the mouse returned to its home tube. At the TPE of the drug, the formalin is injected sub-dermally into the plantar surface of the right hind foot. It is given in a volume of 20 |4,1 with a 27 gauge stainless steel needle attached to a Hamilton syringe. The bevel of the needle is placed facing down toward the skin surface. Following the injection of the formalin each animal is observed for the first 2 min of 5-min epochs until 45 min have elapsed since the administration of the test drug. The cumulative length of licking for each 2-min time period is measured. An animal receiving the equivalent volume of vehicle is alienated with each mouse given the test drug (n=8, per group). Animals are humanely euthanized by $CO_2$ inhalation immediately following the conclusion of the experiment. The area under the curve (AUG) is calculated for both the acute and inflammatory phases of the licking response for individual animals in both the test and control groups. The percent of control AUG for drug-treated animal groups is determined using the Graph-Pad Prism Version 3.03. The total AUG for each phase of the test group is also calculated and converted to percentage of total AUG of control for each phase. The average and S.E.M. for both the drug treated and control percentages are calculated and tested for significant difference. An effect is considered significantly different from the control is p<0.05.

Exemplary compounds of the application were effective in significantly reducing the nociceptive responses, particularly during the second phase of formalin test. For example, compound I(B) at dose 41 mg/kg by i.p. route produced a significant decrease in the number of paw licks. This effect was most pronounced in the second (late) phase as defined by the % inhibition compared to vehicle controls.

Example 11: Sciatic Ligation Model in Rats
(Neuropathic Pain)

Partial Ligation of the Sciatic Nerve:

Animals will be anesthetized with sodium pentobarbital and the depth of anesthesia monitored by their response to a tail pinch and observation of the depth of respiration. Sterile technique will be used throughout the surgery. The upper thigh will be shaved and wiped off with ethanol and betadine. A small incision will then be made in the skin. The underlying muscle of the upper thigh will be separated and the sciatic nerve exposed. The nerve is separated from the surrounding connective tissue and slightly elevated by a pair of fine, curved forceps. Approximately ⅓ to ½ of the nerve is tied off by passing a needle (7.0) and nylon suture through the nerve. The muscle and skin incision are closed off separately with 5.0 suture and the animals kept warm until they have recovered from the anesthesia. This procedure is routinely done on the right side (ipsilateral) while a sham surgery is performed on the left hind leg (contralateral). The latter involves a similar procedure with the exception that the sciatic nerve on this side is only exposed. The rats will be closely monitored daily for the development of infection or untoward effects of the surgery in which case the animals will be immediately euthanized.

After an appropriate time for recovery (7 days) the animals will be tested for the development of mechanical allodynia (abnormal response to a non-noxious stimulus). The animals are each put in a bottomless plexiglass box placed on a wire mesh (¼") platform. After 30-60 minutes in which to acclimate, a baseline mechanical sensitivity is determined. This procedure is done by applying a series of calibrated Von Frey fibers perpendicularly to the plantar surface of each hind paw and holding it there for about 6 sees with enough force to slightly bend the fiber. After a positive response (withdrawal of the foot) is noted a weaker fiber is applied. This is repeated until a 50% threshold for withdrawal can be determined.

The allodynic threshold is then redetermined after intraperitoneal administration of an investigational AED. Testing will be conducted at the time-to-peak effect of the AED as determined in the acute seizure model (Z. Seltzer et al. *Pain* 43 1990, 205-218).

Exemplary compounds of the application were effective in significantly reducing the nociceptive responses, particularly during the second phase of formalin test. For compound I(B) (60 mg/kg i.p.) produced a significant decrease in the mechanical allodynia compared to vehicle controls.

Example 12: Spinal Nerve Injury (SNI) Model
(Neuropathic Pain)

The SNI model of neuropathic pain was developed in rats using the procedure described by Decostered and Woolf, *Pain* 2000, 87: 149-158. Under isoflurane anesthesia, the skin on the lateral surface of the thigh was incised and a section was made directly through the biceps femoris muscle exposing the sciatic nerve and its three terminal branches: the sural, common peroneal and tibial nerves. The common peroneal and the tibial nerves were tight-ligated with 6-0 suture and sectioned distal to the ligation, removing 2-4 mm of the distal nerve stump. Extreme care was taken to avoid any contact with or stretching of the intact sural nerve. Following surgery, hemostasis was confirmed and the muscles were sutured in layers using 4-0 suture and the skin was closed with 4-0 suture and metal clips.

Male, Sprague-Dawley rats were used. Testing of compounds was done 21 days post-operatively. After initial basal readings were taken, the test compound or vehicle was administered. The readings were taken again 30, 60 and 180 min after the compound/vehicle administration. Both the control (uninjured) and the SNI paw were tested. The presence of mechanical allodynia was assessed using the Dynamic Plantar Aesthesiometer (Ugo Basile, Italy) which is a modified version of the Von Frey Hair test. In this, a test filament is positioned below the animal's hind paw and the unit is activated which causes the filament to move up and touch the plantar surface of the hind paw. Increasing force is applied to the paw via the filament. When the animal withdraws its paw, the unit is inactivated automatically and the threshold force required to elicit the paw withdrawal is displayed. A single reading was taken per timepoint. The cut-off force was set at 50 g. The tests were done on both the non-injured (control) and the injured (SNI) paw. Pilot studies showed the presence of mechanical allodynia 7 days after the surgery and lasted up to 4 weeks (end of the test period).

Cold allodynia was assessed by using the acetone test. In this test, 25 µl of acetone is sprayed on to the plantar surface of the hind paw. Evaporation of acetone causes cooling of the skin. The cold stimulus sets up nociceptive responses from the injured paw as evidenced by paw lifting, paw licking and grooming. The duration of the nociceptive responses is noted. Similar stimulus to the uninjured (control) paw usually does not elicit nociceptive responses.

In the case of the SNI model (Von Frey Hair test), the maximum reversal possible was computed as Percent Maximum Possible Effect (MPE) (e.g. Stohr et al, *Eur. J. Pharmacol.* 2006, 10: 241-249).

In the SNI model of neuropathic pain, compound I(B) at a dose of 60 mg/kg i.p. was effective at reducing the mechanical allodynia evident in the denervated paw as measured using the Von Frey test. Cold allodynia in the neuropathic rats was also significantly reduced by this compound.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A compound of Formula (I), or a pharmaceutically acceptable salt, solvate, tautomer or optical isomer, or combination thereof:

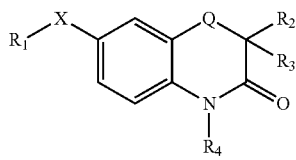

Formula (I)

wherein:
$R_1$ is alkylene-phenyl substituted in the para position with $R_5$;
$R_2$ and $R_3$ are each independently selected from the group consisting of hydrogen and fluorine;
$R_4$ is hydrogen;
X is O;
Q is selected from $CH_2$, O, and $NR_7$;
$R_5$ is fluoroalkoxy; and
$R_7$ is selected from the group consisting of H, $C_1$-$C_4$ alkyl, and $C_1$-$C_4$ haloalkyl.

2. The compound of claim 1, wherein Q is selected from O and $NR_7$.
3. The compound of claim 2, wherein $R_7$ is selected from the group consisting of hydrogen and $CH_3$.
4. The compound of claim 1, wherein Q is O.
5. The compound of claim 1, wherein $R_5$ is difluoromethoxy or trifluoromethoxy.
6. The compound of claim 1, wherein $R_2$ and $R_3$ are both F.
7. The compound of claim 1, selected from:
   7-(4-difluoromethoxy-benzyloxy)-4H-benzo[1,4]oxazin-3-one; and
   7-(4-trifluoromethoxy-benzyloxy)-4H-benzo[1,4]oxazin-3-one; or
   a pharmaceutically-acceptable salt, solvate, tautomer or optical isomer, or combination thereof.
8. A compound of the formula:

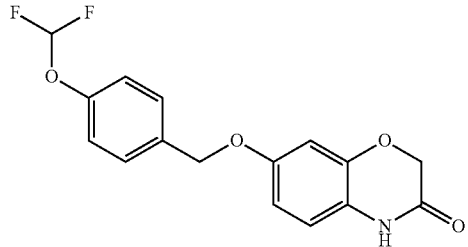 [SMILES: O=C1COc2cc(OCc3ccc(OC(F)F)cc3)ccc2N1]

or a pharmaceutically-acceptable solvate or tautomer, or combination thereof.

9. A pharmaceutical composition comprising a compound according to claim 1 and at least one pharmaceutically acceptable carrier and/or excipient.
10. A method for treating ( . . . ) tardive dyskinesia and anxiety in a mammal in need thereof, comprising administering to the mammal a therapeutically effective amount of a compound according to claim 1.
11. The method according to claim 10, wherein the mammal is a human.
12. A method for treating ( . . . ) tardive dyskinesia and anxiety in a mammal in need thereof, comprising administering to the mammal a therapeutically effective amount of a compound according to claim 8.
13. The method according to claim 12, wherein the mammal is a human.
14. The compound of claim 1, wherein $R_5$ is $OCHF_2$.
15. The compound of claim 1, wherein $R_5$ is $OCF_3$.
16. The compound of claim 1, wherein $R_2$ and $R_3$ are both H.
17. The compound of claim 1, wherein one of $R_2$ and $R_3$ is F and the other is H.

* * * * *

UNITED STATES PATENT AND TRADEMARK OFFICE
CERTIFICATE OF CORRECTION

PATENT NO. : 10,428,030 B2
APPLICATION NO. : 15/771465
DATED : October 1, 2019
INVENTOR(S) : Abdelmalik Slassi It is certified that error appears in the above-identified patent and that said Letters Patent is hereby corrected as shown below:

In the Claims

Column 43, Line 52, Claim 1 "$R^5$ is fluoroalkoxy" should read -- $R^5$ is $C_1 – C_4$ fluoroalkoxy --.

Column 44, Line 36, Claim 10 "(...)" should read -- at least one of epilepsy, neuropathic pain, acute and chronic inflammatory pain, migraine, --.

Column 44, Line 42, Claim 12 "(...)" should read -- at least one of epilepsy, neuropathic pain, acute and chronic inflammatory pain, migraine, --.

Signed and Sealed this
Seventh Day of July, 2020

Andrei Iancu
*Director of the United States Patent and Trademark Office*